(12) United States Patent
Green et al.

(10) Patent No.: US 11,773,430 B2
(45) Date of Patent: Oct. 3, 2023

(54) UNIMOLECULAR APTAMER-BASED SENSORS FOR PATHOGEN DETECTION

(71) Applicant: Arizona Board of Regents on behalf of Arizona State University, Scottsdale, AZ (US)

(72) Inventors: Alexander Green, Scottsdale, AZ (US); Duo Ma, Tempe, AZ (US); Anli Tang, Gilbert, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1119 days.

(21) Appl. No.: 16/342,722

(22) PCT Filed: Oct. 17, 2017

(86) PCT No.: PCT/US2017/056960
§ 371 (c)(1),
(2) Date: Apr. 17, 2019

(87) PCT Pub. No.: WO2018/075502
PCT Pub. Date: Apr. 26, 2018

(65) Prior Publication Data
US 2019/0256898 A1 Aug. 22, 2019

Related U.S. Application Data

(60) Provisional application No. 62/408,846, filed on Oct. 17, 2016.

(51) Int. Cl.
*C12Q 1/6825* (2018.01)
*C12Q 1/6816* (2018.01)

(52) U.S. Cl.
CPC ......... *C12Q 1/6825* (2013.01); *C12Q 1/6816* (2013.01); *Y02A 50/30* (2018.01)

(58) Field of Classification Search
CPC .............................................. C12Q 2525/205
See application file for complete search history.

(56) References Cited

U.S. PATENT DOCUMENTS

| 6,294,365 | B1 | 9/2001 | De Rosier | |
|---|---|---|---|---|
| 2016/0076083 | A1* | 3/2016 | Ellington | C12Q 1/6806 435/6.12 |
| 2016/0153036 | A1 | 6/2016 | Chen et al. | |
| 2019/0071737 | A1 | 3/2019 | Green | |
| 2019/0185856 | A1 | 6/2019 | Green | |
| 2019/0218624 | A1 | 7/2019 | Green | |
| 2019/0276901 | A1 | 9/2019 | Green | |
| 2019/0285620 | A1 | 9/2019 | Green | |

FOREIGN PATENT DOCUMENTS

| WO | 2017147585 A1 | 8/2017 |
|---|---|---|
| WO | 2017205668 A1 | 11/2017 |
| WO | 2018026762 A1 | 2/2018 |
| WO | 2018026765 A1 | 2/2018 |
| WO | 2018027177 A1 | 2/2018 |
| WO | 2018093898 A1 | 5/2018 |
| WO | 2018112350 A1 | 6/2018 |
| WO | 2018187687 A1 | 10/2018 |

OTHER PUBLICATIONS

Oishi, M. et al., Enzyme-free fluorescent-amplified aptasensors based on target-responsive DNA strand displacement via toehold-mediated click chemical ligation, Chem. Comm., vol. 50, pp. 991-993 (Year: 2014).*
Mohammadi-Yeganeh, S. et al., Molecular beacon probes-base multiplex NASBA Real-time for detection of HIV-1 and HCV, Iranian J. Microbiol., vol. 4, pp. 47-54 (Year: 2012).*
Akter, F., et al. (2015). RNA signal amplifier circuit with integrated fluorescence output. ACS synthetic biology 4, 655-658.
Babendure, J. R., et al. "Aptamers switch on fluorescence of triphenylmethane dyes." Journal of the American Chemical Society 125.48 (2003): 14716-14717.
Bhadra, S., et al. (2014). A Spinach molecular beacon triggered by strand displacement. RNA 20, 1183-1194.
Filonov, G. S., et al(2014). Broccoli: Rapid Selection of an RNA Mimic of Green Fluorescent Protein by Fluorescence-Based Selection and Directed Evolution. J. Am. Chem. Soc. Journal of the American Chemical Society, 136(46), 16299-16308.
Golub, E., et al. (2011). Hemin/G-quadruplexes as DNAzymes for the fluorescent detection of DNA, aptamer-thrombin complexes, and probing the activity of glucose oxidase. Analyst 136, 4397-4401.
Green, A., et al. (2014). Toehold Switches: De-Novo-Designed Regulators of Gene Expression. Cell, 159(4), 925-939.
Kikuchi, N., et al. (2016). Split Spinach Aptamer for Highly Selective Recognition of DNA and RNA at Ambient Temperatures. ChemBioChem.
Kolpashchikov, D. M. (2008). Split DNA Enzyme for Visual Single Nucleotide Polymorphism Typing. J. Am. Chem. Soc. Journal of the American Chemical Society, 130(10), 2934-2935.
Liu, Q., et al. (2016). Two-stage sample-to-answer system based on nucleic acid amplification approach for detection of malaria parasites. Biosensors and Bioelectronics, 82, 1-8.
Liu, Wei, et al. "Polymerase Spiral Reaction (PSR): A novel isothermal nucleic acid amplification method." Scientific reports 5 (2015): 12723.
Nakahara, K., et al. (1998). Inosine 5'-triphosphate can dramatically increase the yield of NASBA products targeting GC-rich and intramolecular base-paired viroid RNA. Nucleic Acids Research, 26(7), 1854-1855.

(Continued)

*Primary Examiner* — Teresa E Strzelecka
(74) *Attorney, Agent, or Firm* — Quarles & Brady LLP

(57) ABSTRACT

Methods and compositions for detecting the presence of a pathogen are described. In particular, this document provides a method of detecting a pathogen-associated nucleic acid in a biological sample of a subject, where the method comprises using one or more unimolecular aptamer-based sensors comprising an aptamer-fluorophore complex and an amplification step to detect the pathogen-associated nucleic acid. Methods specific for detecting the presence of malaria and other mosquito-borne virus infections are also provided.

12 Claims, 26 Drawing Sheets

Specification includes a Sequence Listing.

(56) References Cited

OTHER PUBLICATIONS

Paige, J. S.; et al. (2011). RNA mimics of green fluorescent protein. Science, 333, 642.
Pardee, K., et al. (2016). Rapid, Low-Cost Detection of Zika Virus Using Programmable Biomolecular Components. Cell, 165(5), 1255-1266.
Rogers, T.A., et al. (2015). Fluorescent Monitoring of RNA Assembly and Processing Using the Split-Spinach Aptamer. ACS synthetic biology 4, 162-166.
Salgueiro, P., et al. (2016). Genetic diversity and population structure of Plasmodium falciparum over space and time in an African archipelago. Infection, Genetics and Evolution, 43, 252-260.
Sato, S-I, et al. "Live-cell imaging of endogenous mRNAs with a small molecule." Angewandte Chemie International Edition 54.6 (2015): 1855-1858.
Schneider, P., et al. (2004). Quantification of Plasmodium falciparum gametocytes in differential stages of development by quantitative nucleic acid sequence-based amplification. Molecular and Biochemical Parasitology, 137(1), 35-41.
Schneider, P., et al. (2005). Real-Time Nucleic Acid Sequence-Based Amplification Is More Convenient than Real-Time PCR for Quantification of Plasmodium falciparum. Journal of Clinical Microbiology, 43(1), 402-405.
Schneider, P., et al. (2006). (Sub)microscopic Plasmodium falciparum gametocytaemia in Kenyan children after treatment with sulphadoxine-pyrimethamine monotherapy or in combination with artesunate. International Journal for Parasitology, 36(4), 403-408.
Song, W., et al. "Plug-and-play fluorophores extend the spectral properties of Spinach." Journal of the American Chemical Society 136.4 (2014): 1198-1201.
Strack, R. L., et al. "A superfolding Spinach2 reveals the dynamic nature of trinucleotide repeat-containing RNA." Nature methods 10.12 (2013): 1219.
Xiao, Y., et al. (2004). Catalytic Beacons for the Detection of DNA and Telomerase Activity. Journal of the American Chemical Society 126, 7430-7431.
Yan, L., et al. (2014). A G-quadruplex DNA-based, Label-Free and Ultrasensitive Strategy for microRNA Detection. Scientific Reports 4, 7400.
You, M., et al. (2015). Structure and Mechanism of RNA Mimics of Green Fluorescent Protein. Annu. Rev. Biophys. Annual Review of Biophysics, 44(1), 187-206.
Zadeh, J.N., et al. (2010). NUPACK: Analysis and design of nucleic acid systems. J. Comput. Chem. 32, 170-173.
Zhang, Z., et al. (2012). Fluorescence Detection of DNA, Adenosine-5'-Triphosphate (ATP), and Telomerase Activity by Zinc(II)-Protoporphyrin IX/G-Quadruplex Labels. Analytical Chemistry 84, 4789-4797.
U.S. Appl. No. 16/245,984.
U.S. Appl. No. 16/303,937.
U.S. Appl. No. 16/322,719.
U.S. Appl. No. 16/349,752.
U.S. Appl. No. 16/468,846.
U.S. Appl. No. 16/603,338.
International Search Report and Written Opinion for International Patent Application No. PCT/US2017/056960 dated Oct. 17, 2017.
Feng et al. "Hairpin assembly circuit-based fluorescence cooperative amplification strategy for enzyme-free and label-free detection of small molecule." Talanta 143 (2015): 101-106. [located online Feb. 5, 2018 at http:/lwxjs.chinayyhg.com/upload/Files/20160816125538798/101-106.pdf] entire document, especially abstract.

* cited by examiner

FIGS. 3A-3D
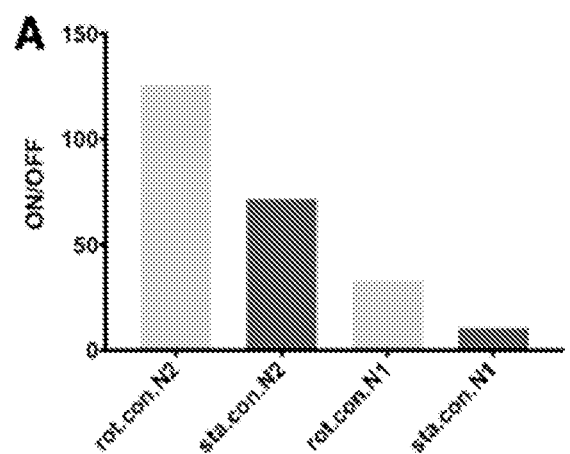
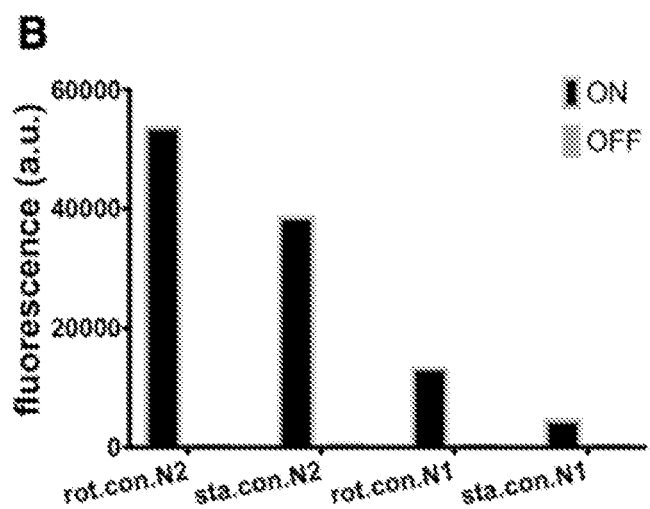

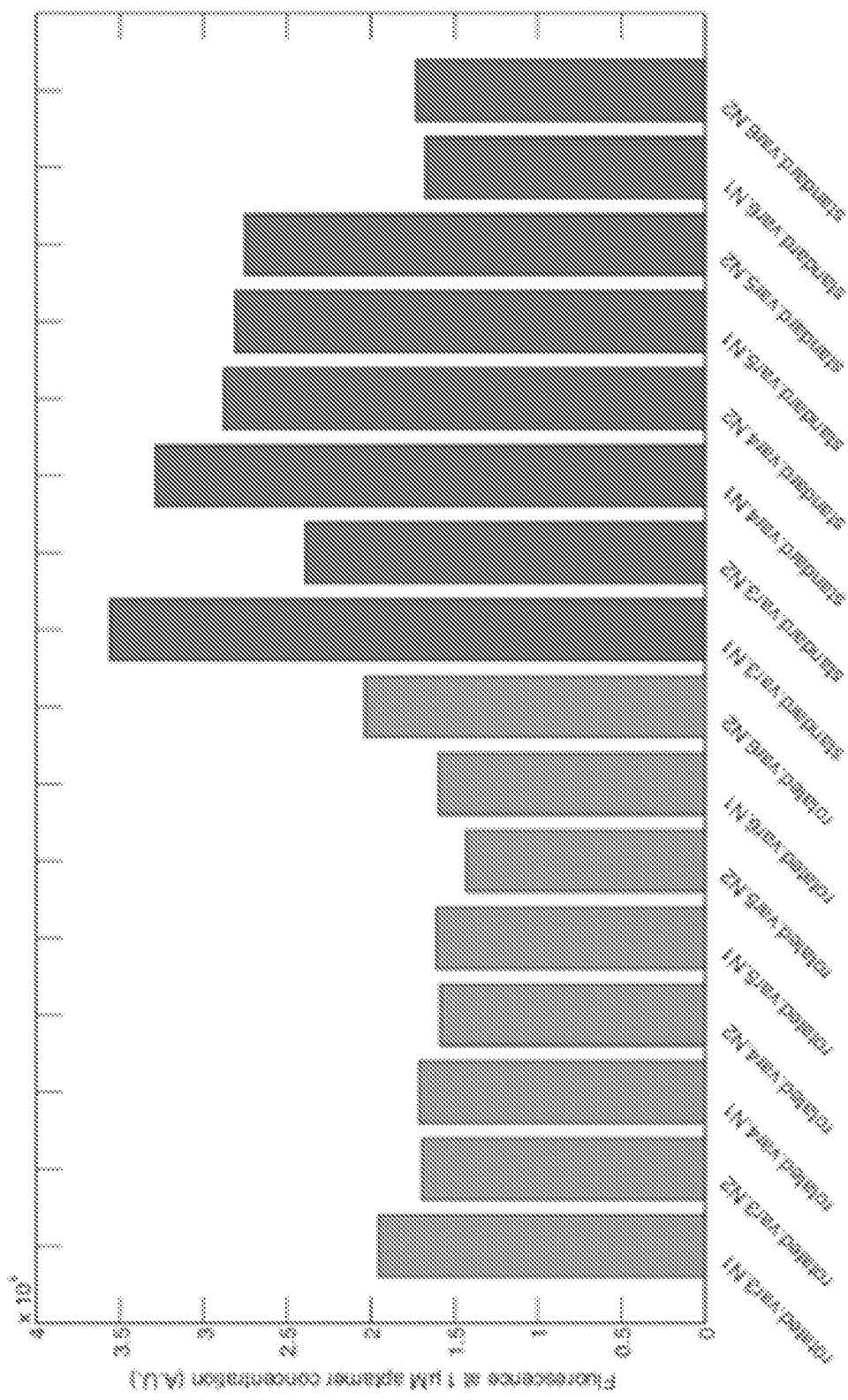
FIGS. 3A-3D, CONTINUED

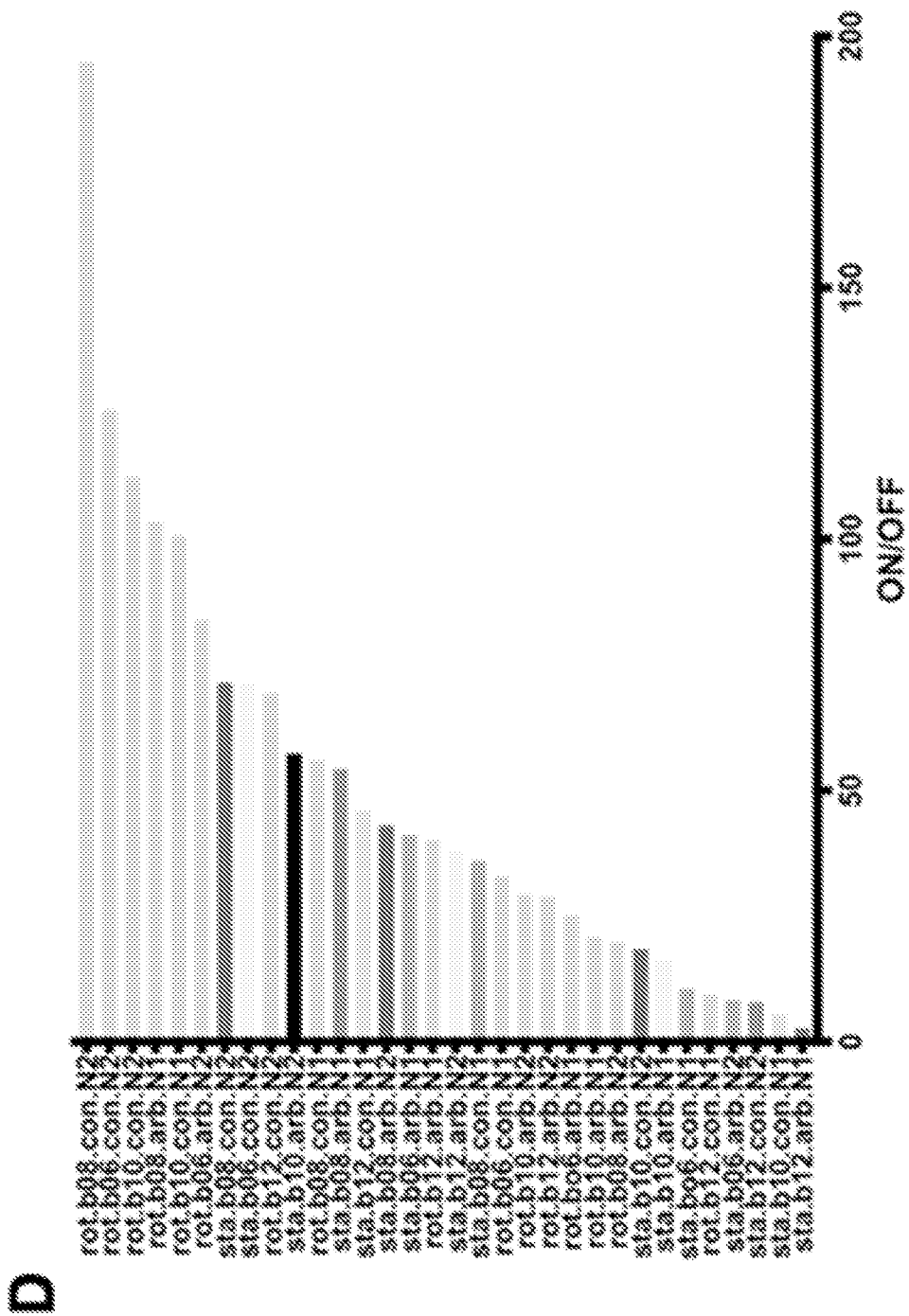
FIGS. 3A-3D, CONTINUED

FIGS. 4A-4E, CONTINUED
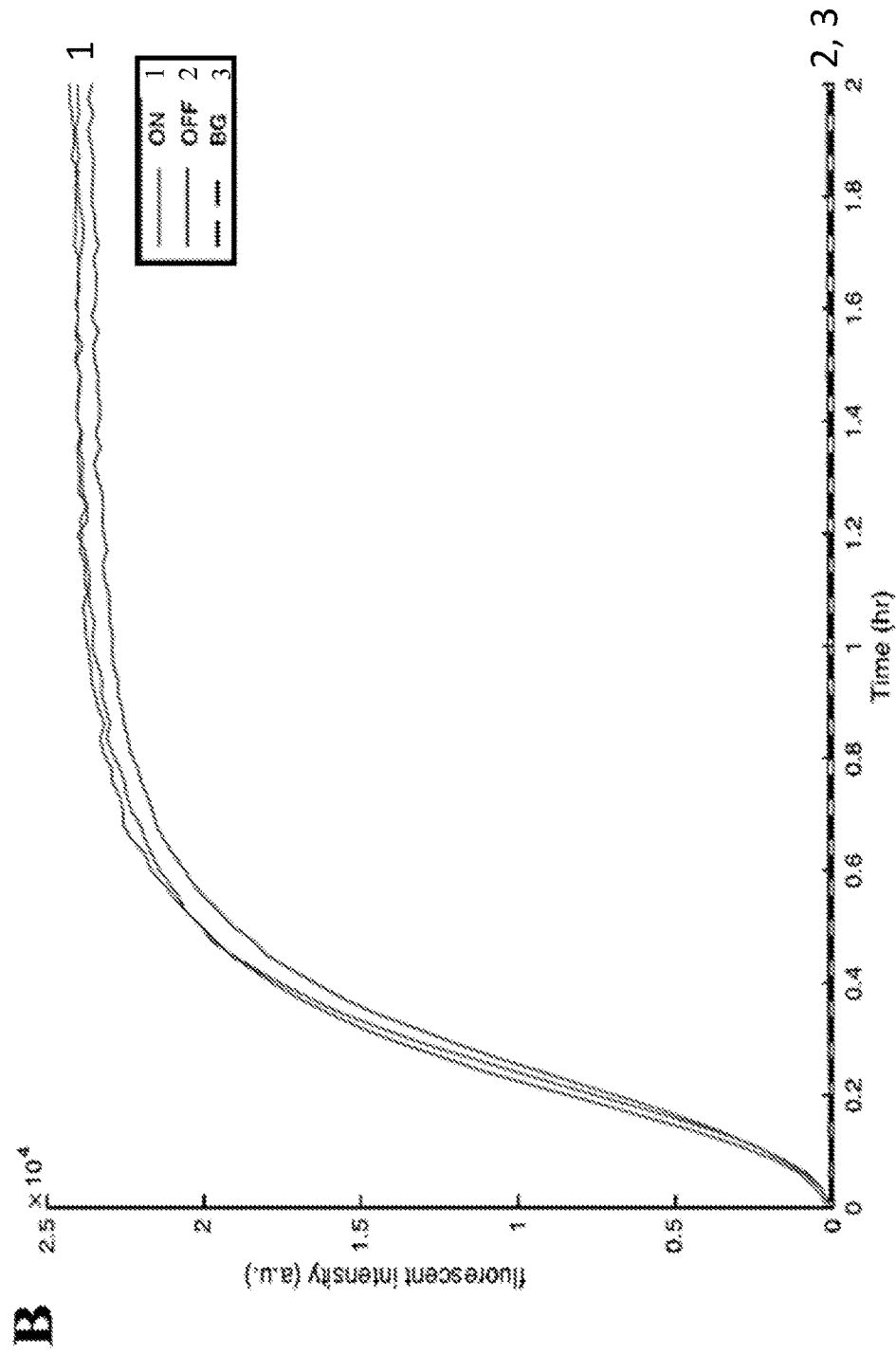

FIGS. 4A-4E, CONTINUED
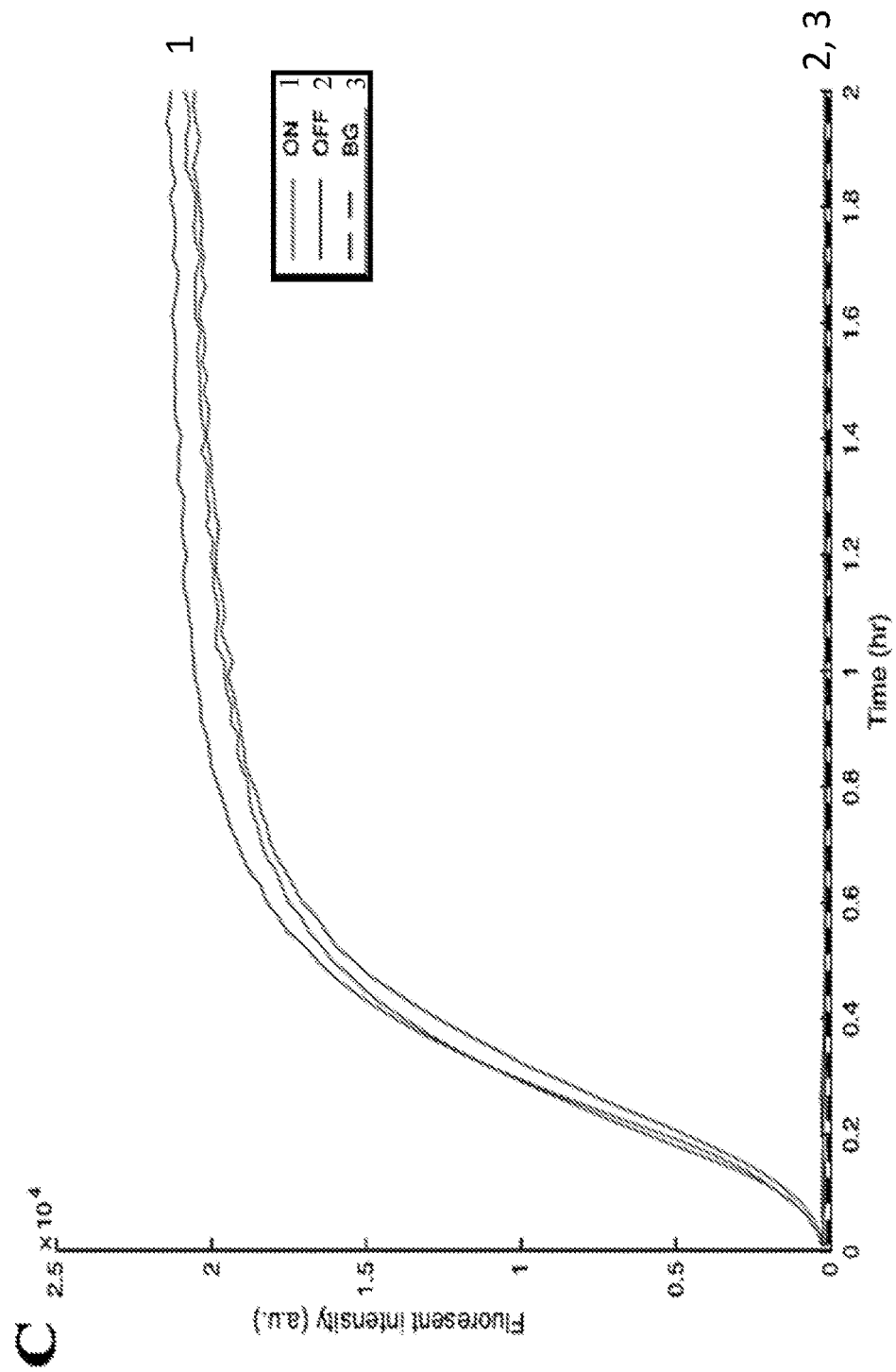

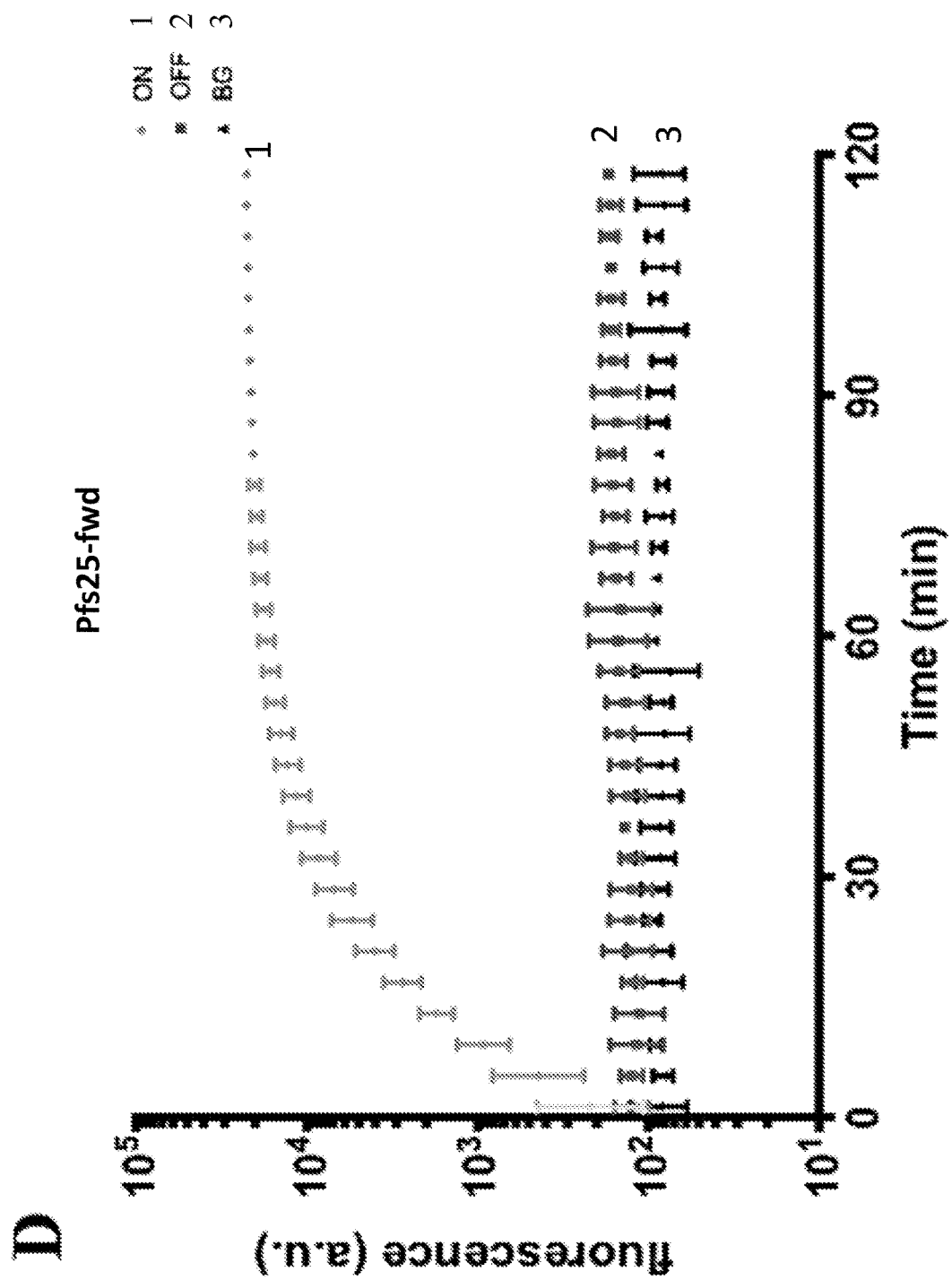
FIGS. 4A-4E, CONTINUED

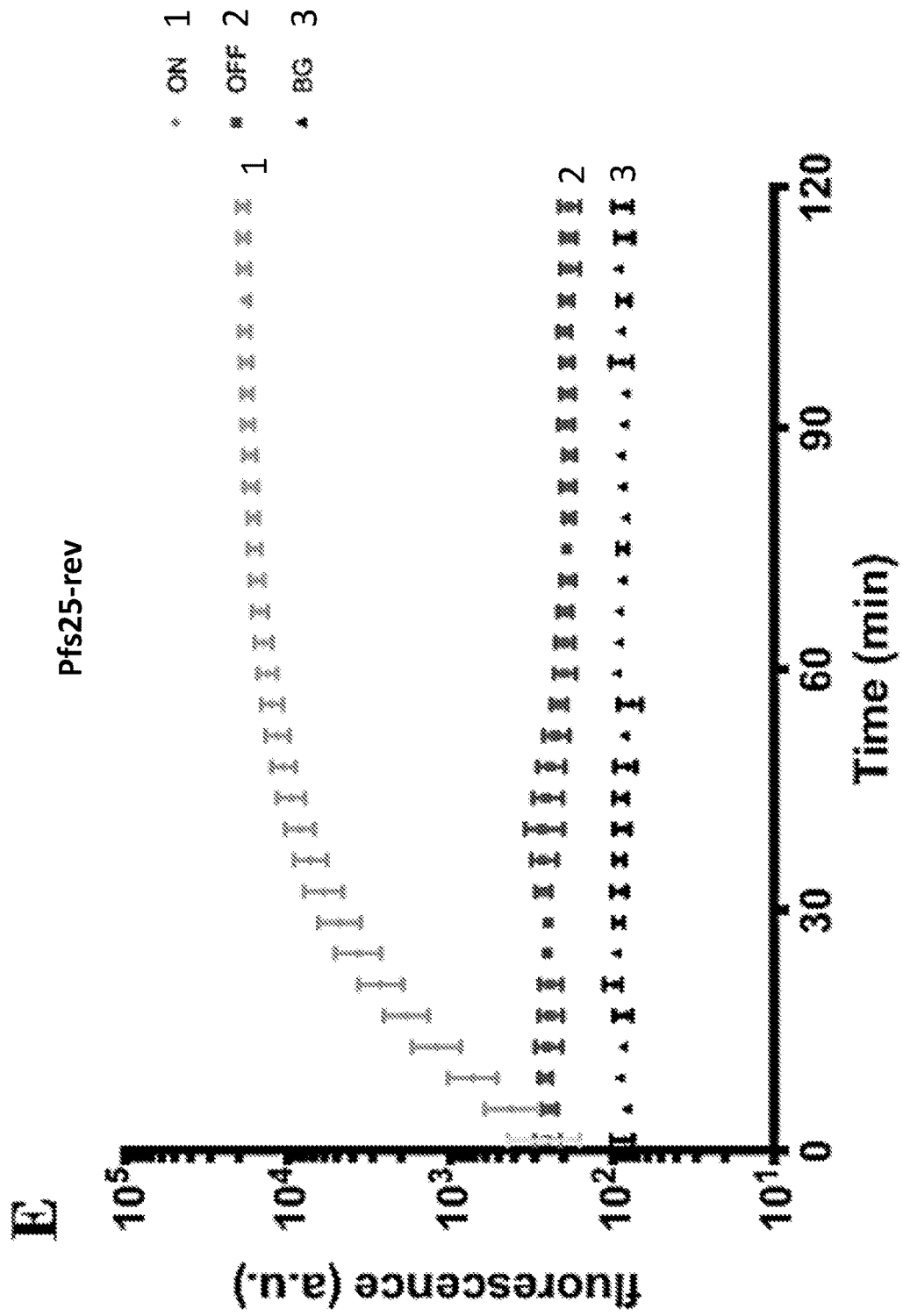
FIGS. 4A-4E, CONTINUED

FIGS. 10A-10D, CONTINUED
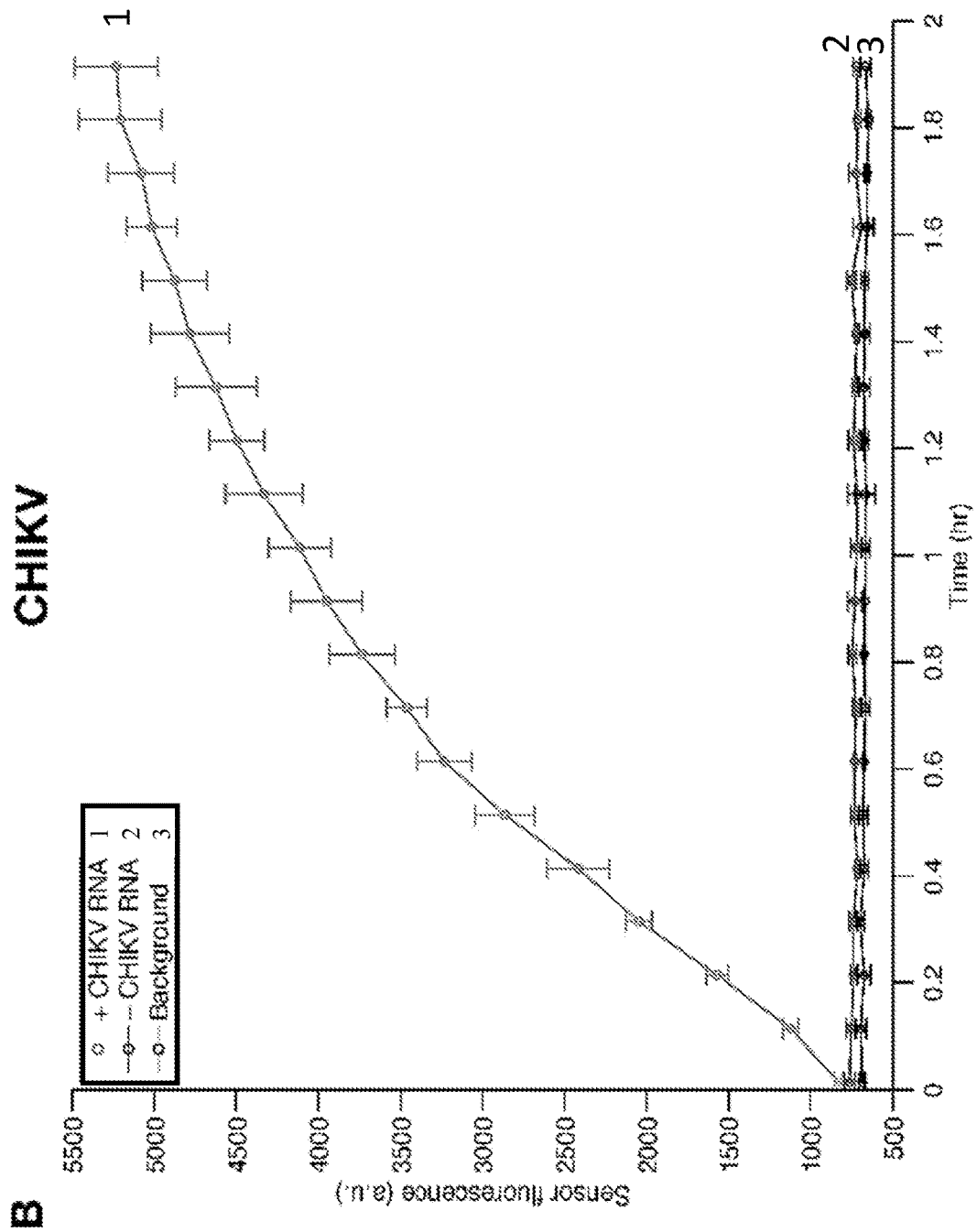

FIGS. 10A-10D, CONTINUED
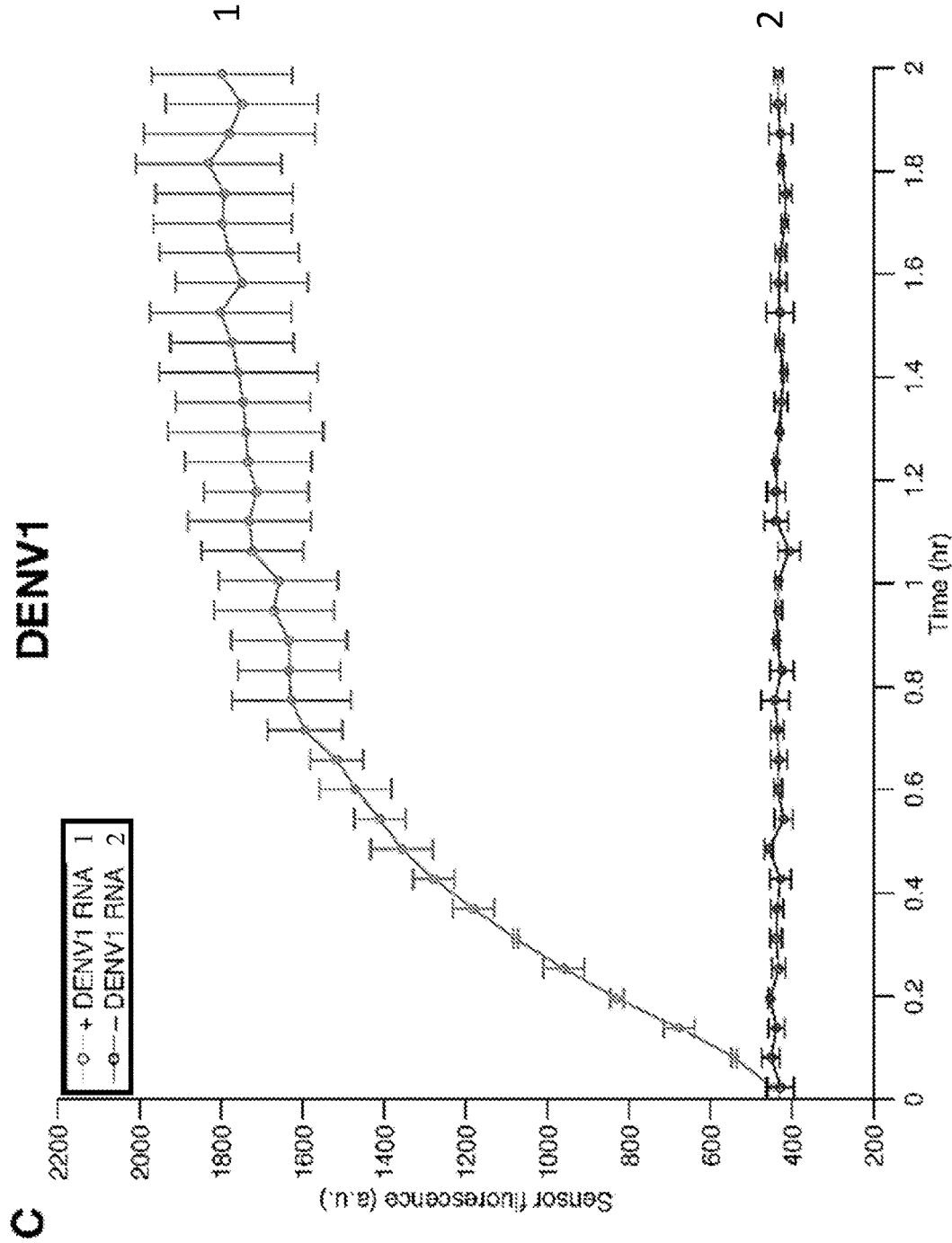

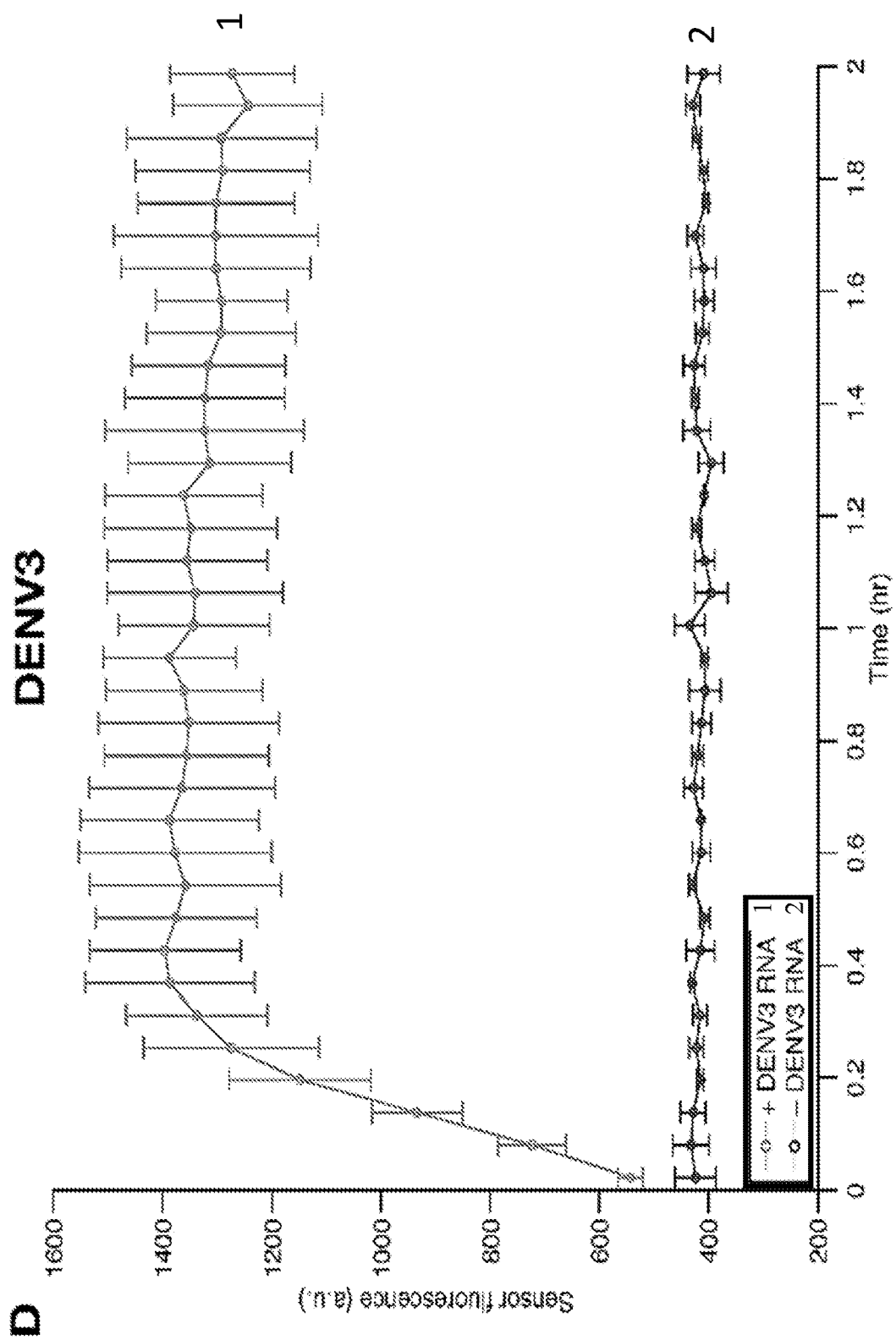
FIGS. 10A-10D, CONTINUED

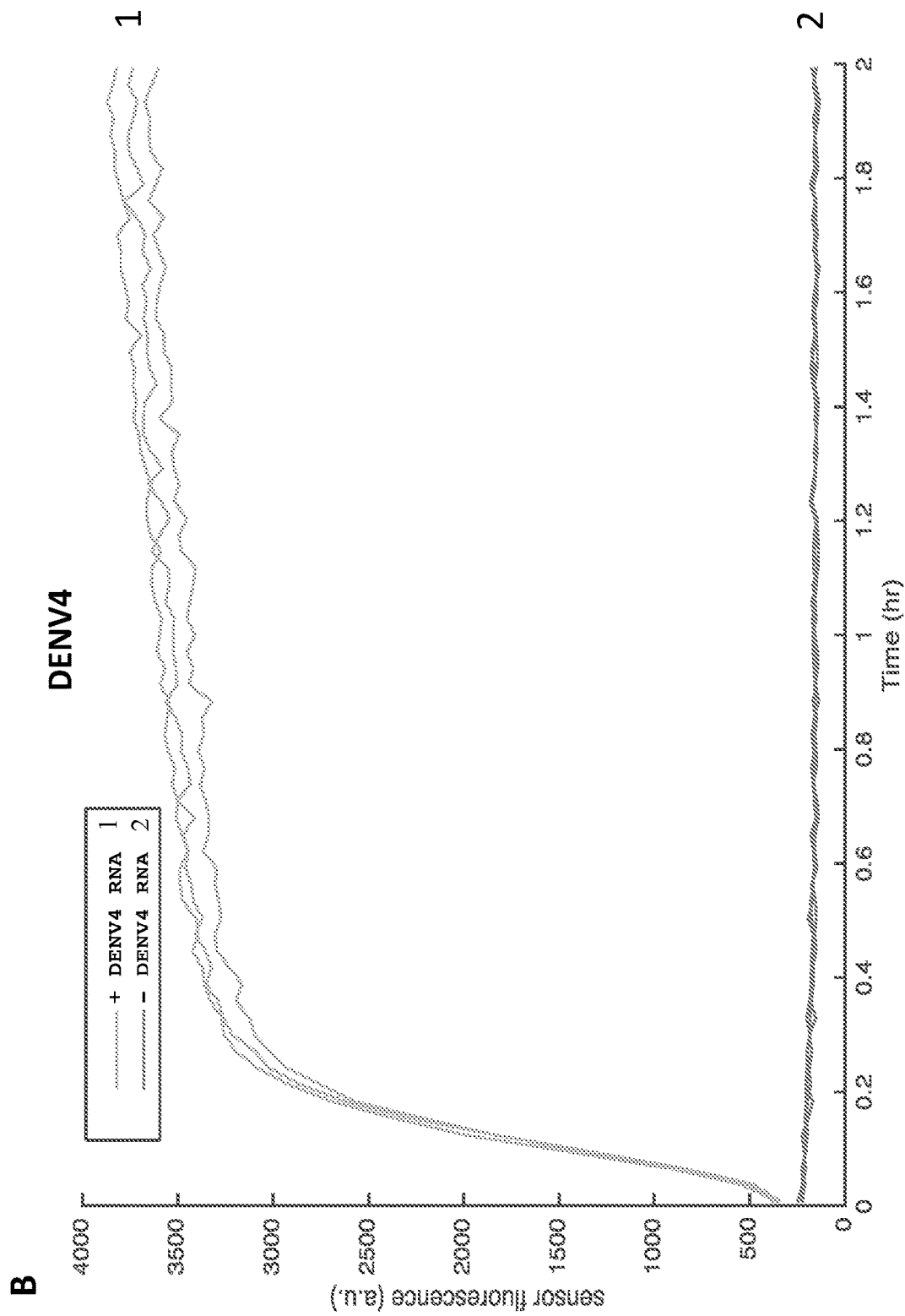
FIGS. 12A-12B, CONTINUED

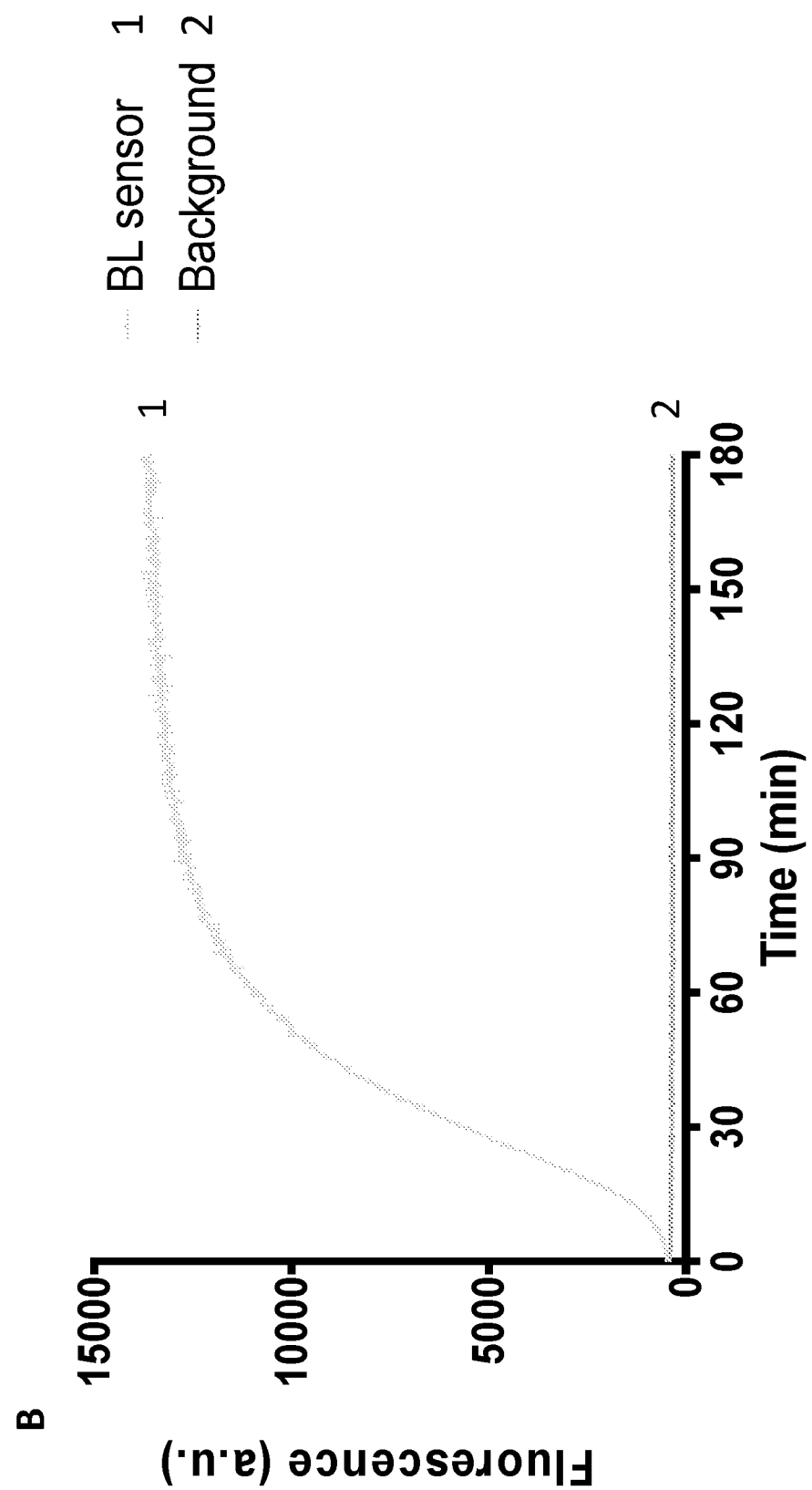
FIGS. 14A-14C, CONTINUED

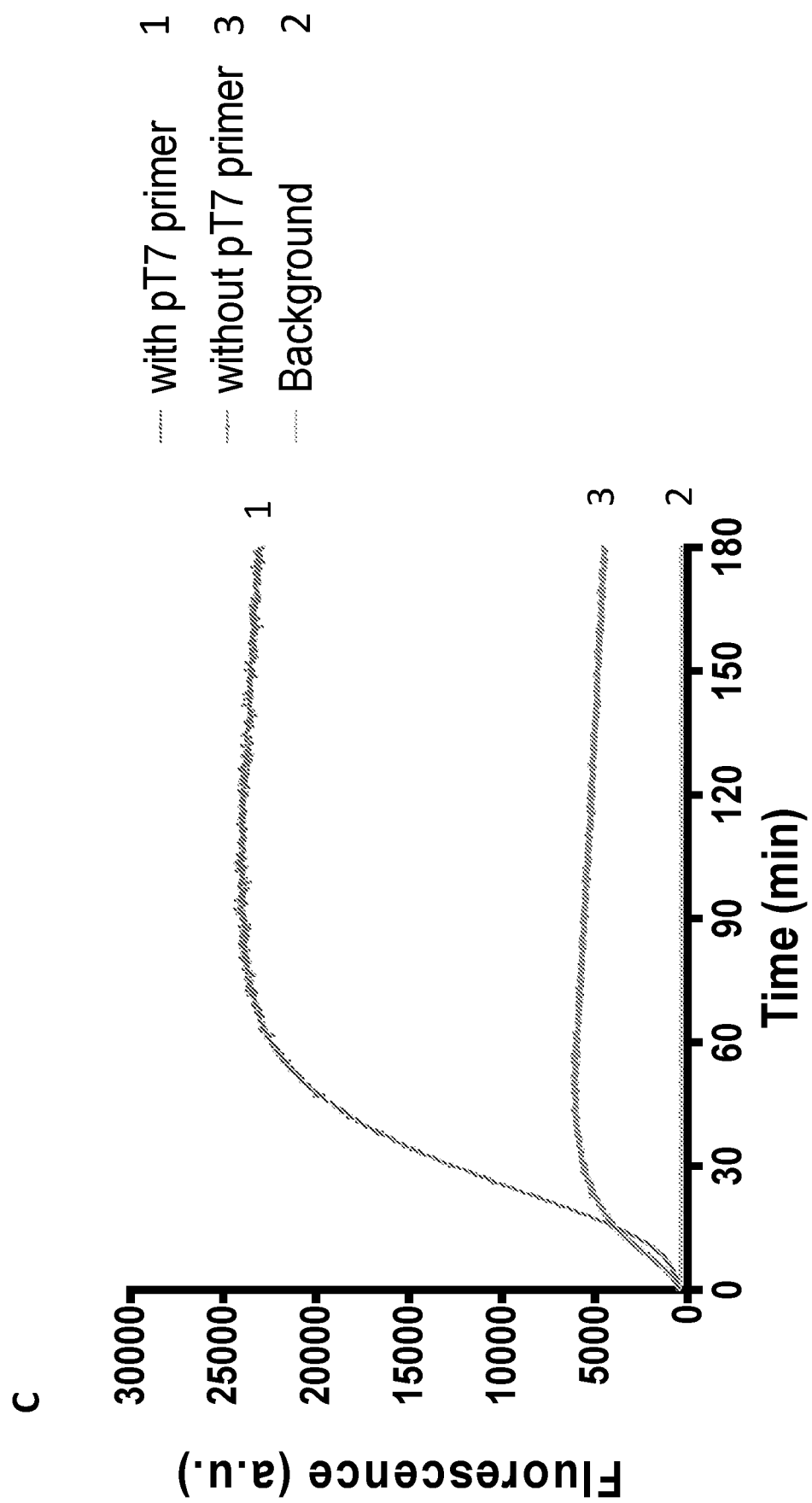
FIGS. 14A-14C, CONTINUED

UNIMOLECULAR APTAMER-BASED SENSORS FOR PATHOGEN DETECTION

CROSS-REFERENCE TO RELATED APPLICATIONS

This application represents the national stage entry of PCT International Application No. PCT/US2017/056960, filed on Oct. 17, 2017, and, claims priority to U.S. Provisional Application No. 62/408,846, filed Oct. 17, 2016, each of which is incorporated herein by reference as if set forth in its entirety.

STATEMENT REGARDING FEDERALLY SPONSORED RESEARCH OR DEVELOPMENT

This invention was made with government support under GM126892 awarded by National Institutes of Health. The government has certain rights in the invention.

BACKGROUND

Synthetic biology is an emerging discipline that has great potential to respond to global pandemics. The increasing ability of synthetic biologists to repurpose and engineer natural biological components for practical applications has led to new opportunities for molecular diagnostics.

The ability to detect nucleic acids specifically, quickly, and at low cost is critical for the development of point-of-care diagnostics. However, there exist few methods that can simultaneously satisfy these requirements as a result of the challenge of establishing specific nucleic acid interactions at low temperatures, the costs associated with synthesizing modified nucleic acids, and the limited number of reliable low-cost readout methods. Accordingly, there remains a need in the art for improved methods and devices for the specific and rapid detection of pathogen RNA sequences and for accurate pathogen identification. In particular, there remains a need in the art for improved detection methods and devices that provide fast turn on rates, high dynamic range, and can be produced enzymatically at low costs. Development of such systems could prove critically important for the development of low-cost point-of-care nucleic acid tests for specific and rapid detection of pathogen RNAs and for accurate pathogen identification.

SUMMARY OF THE DISCLOSURE

Provided herein are unimolecular aptamer-based sensors and methods of using the same for sensitive, specific, and reliable detection of a target nucleic of interest. In particular, provided herein are unimolecular aptasensor designs that trigger the formation of functional aptamers in response to the binding of pathogen target nucleic acids with arbitrary sequences.

In a first aspect, provided herein is a method of detecting a target nucleic acid. The method can comprise or consist essentially of (a) obtaining nucleic acids from a biological sample of a subject; (b) amplifying the nucleic acids using isothermal amplification; (c) contacting the amplified nucleic acids to a unimolecular aptamer-based sensor, wherein the unimolecular aptamer-based sensor is a nucleic acid sequence comprising one or more single-stranded toehold sequence domains that are complementary to the target nucleic acid, a fully or partially double-stranded stem domain, a loop domain, and an aptamer-ligand complex, and wherein the contacting occurs under conditions that promote activation of the aptamer-ligand complex in the presence of the target nucleic acid; and (d) detecting fluorescence emitted or color produced by the activated aptamer-ligand complex as an indicator that the target nucleic acid is present in the sample. The aptamer-ligand complex can comprise an aptamer selected from the group consisting of Broccoli, Spinach2, Carrot, Radish, a G-quadruplex-containing aptamer, and a malachite green binding aptamer. The toehold sequence domain can be complementary in sequence to a naturally occurring RNA or a naturally occurring DNA. The toehold sequence domain can be complementary in sequence to a non-naturally occurring RNA or a non-naturally occurring DNA. The sample can be a biological sample selected from the group consisting of blood, plasma, serum, urine, saliva, tissue, cell, organ, and organism, or a portion thereof. The isothermal amplification can be a method selected from the group consisting of NASBA (nucleic acid sequence-based amplification), LAMP (loop-mediated isothermal amplification), and RPA (recombinase polymerase amplification).

In another aspect, provided herein is a method of detecting presence of pathogen-associated nucleic acid in a sample. The method can comprise or consist essentially of (a) obtaining nucleic acids from a biological sample of a subject; (b) amplifying the nucleic acids using isothermal amplification; and (c) contacting the amplified nucleic acids to a unimolecular aptamer-based sensor, wherein the unimolecular aptamer-based sensor is a nucleic acid sequence comprising one or more single-stranded toehold sequence domains that are complementary to the target pathogen-associated nucleic acid, a fully or partially double-stranded stem domain, a loop domain, and an aptamer-ligand complex, and wherein the contacting occurs under conditions that promote activation of the aptamer-ligand complex in the presence of the target pathogen-associated nucleic acid but not in the absence of the pathogen-associated nucleic acid. The aptamer-ligand complex can comprise an aptamer selected from the group consisting of Broccoli, Spinach2, Carrot, Radish, a G-quadruplex-containing aptamer, and a malachite green binding aptamer. The toehold sequence domain can be complementary in sequence to a naturally occurring RNA or a naturally occurring DNA. The isothermal amplification can be a method selected from the group consisting of NASBA, LAMP, and RPA. The sample can be a biological sample selected from the group consisting of blood, plasma, serum, urine, saliva, tissue, cell, organ, and organism, or a portion thereof.

In a further aspect, provided herein is a method of detecting the presence of pathogen-associated nucleic acid in a sample. The method can comprise or consist essentially of (a) obtaining nucleic acids from a biological sample of a subject; and (b) amplifying the obtained nucleic acids using isothermal amplification and simultaneously contacting the nucleic acids being amplified to a unimolecular aptamer-based sensor, wherein the unimolecular aptamer-based sensor is a nucleic acid sequence comprising one or more single-stranded toehold sequence domains that are complementary to the target pathogen-associated nucleic acid, a fully or partially double-stranded stem domain, a loop domain, and an aptamer-ligand complex, wherein the contacting occurs under conditions that promote activation of the aptamer-ligand complex in the presence of the target pathogen-associated nucleic acid but not in the absence of the pathogen-associated nucleic acid.

In another aspect, provided herein is a unimolecular aptamer-based sensor. The sensor can comprise or consist essentially of a synthetic nucleic acid molecule comprising (a) a fully or partially double-stranded stem-forming domain, (b) a toehold domain, (c) a loop-forming domain, and (d) an aptamer sequence, and wherein at least a portion of the synthetic nucleic acid molecule is complementary to a target nucleic acid sequence. The aptamer sequence can be bound to at least one signal-generating ligand. The signal-emitting ligand can generate a fluorescent signal or a colorimetric signal. The aptamer sequence can be split into at least two portions, whereby one portion of the aptamer sequence is located in the loop-forming domain, and a second portion of the aptamer sequence is downstream of the stem-forming domain. The sensor can be configured for binding of the target nucleic acid sequence to the toehold domain and activation of fluorescence emission or production of a visible color in the presence of the target nucleic acid sequence. The sensor can be configured for binding of the target nucleic acid sequence to the toehold domain and formation of a guanine quadruplex in the presence of the target nucleic acid sequence. The stem-forming domain can overlap with at least a portion of the aptamer sequence, and wherein the sensor is configured for binding of the target nucleic acid sequence to the toehold domain and activation of fluorescence emission or production of a visible color in the presence of the target nucleic acid sequence.

In another aspect, provided herein is a device for identifying a pathogen-associated nucleic acid. The device can comprise or consist essentially of a preserved paper test article, wherein the methods described herein are performed using the preserved paper test article. The paper test article can be preserved by freeze-drying.

In a further aspect, provided herein is a kit for detecting a pathogen-associated nucleic acid. The kit can comprise or consist essentially of a plurality of preserved paper test articles, a plurality of unimolecular aptamer-based sensors described herein, and an electronic optical reader.

In another aspect, provided herein is a device for identifying a pathogen-associated nucleic acid. The device can comprise or consist essentially of a preserved test tube article, wherein the methods described herein are performed using the preserved test tube article. The test tube article can be preserved by freeze-drying.

In a further aspect, provided herein is a kit for detecting a pathogen-associated nucleic acid. The kit can comprise or consist essentially of a plurality of preserved test tube articles, a plurality of unimolecular aptamer-based described herein , and an electronic optical reader.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein:

FIGS. 3A-3D present fluorescence and ON/OFF ratios of Broccoli-based sensors and Broccoli sequence variants. (A) ON/OFF ratios from the fluorescence for initial 4 Broccoli-based RNA sensors with conserved aptamer sequences. (B) ON and OFF state fluorescence data for initial 4 Broccoli-based RNA sensors with conserved aptamer sequences. (C) Fluorescence intensities of the Broccoli aptamers with variations in stem sequence. RNA aptamer fluorescence is reported at 1 μM concentration. (D) ON/OFF ratios from the fluorescence for 32 Broccoli-based RNA sensors with stem length variations.

Design 1 features an aptasensor with an extended docking site that is used to initially capture the target RNA. A subsequent toehold-mediated quasi-intramolecular interaction in the target-aptasensor complex enables the domain b to be unwound. Transient unwinding of domain c enables binding of aptamer halves X and Y to activate the aptamer. A single-nucleotide change in the target RNA in domains a* or b* prevents the stem from unwinding and in turn prevents X and Y from interacting. (B) Design 2 is similar to Design 1 (A), except that a downstream c domain is added to the 3' end of the aptasensor. This extra domain encourages complete unwinding of the stem by competing with the c/c* domains for binding and increases the probability of the active aptamer forming.

Figure 9:
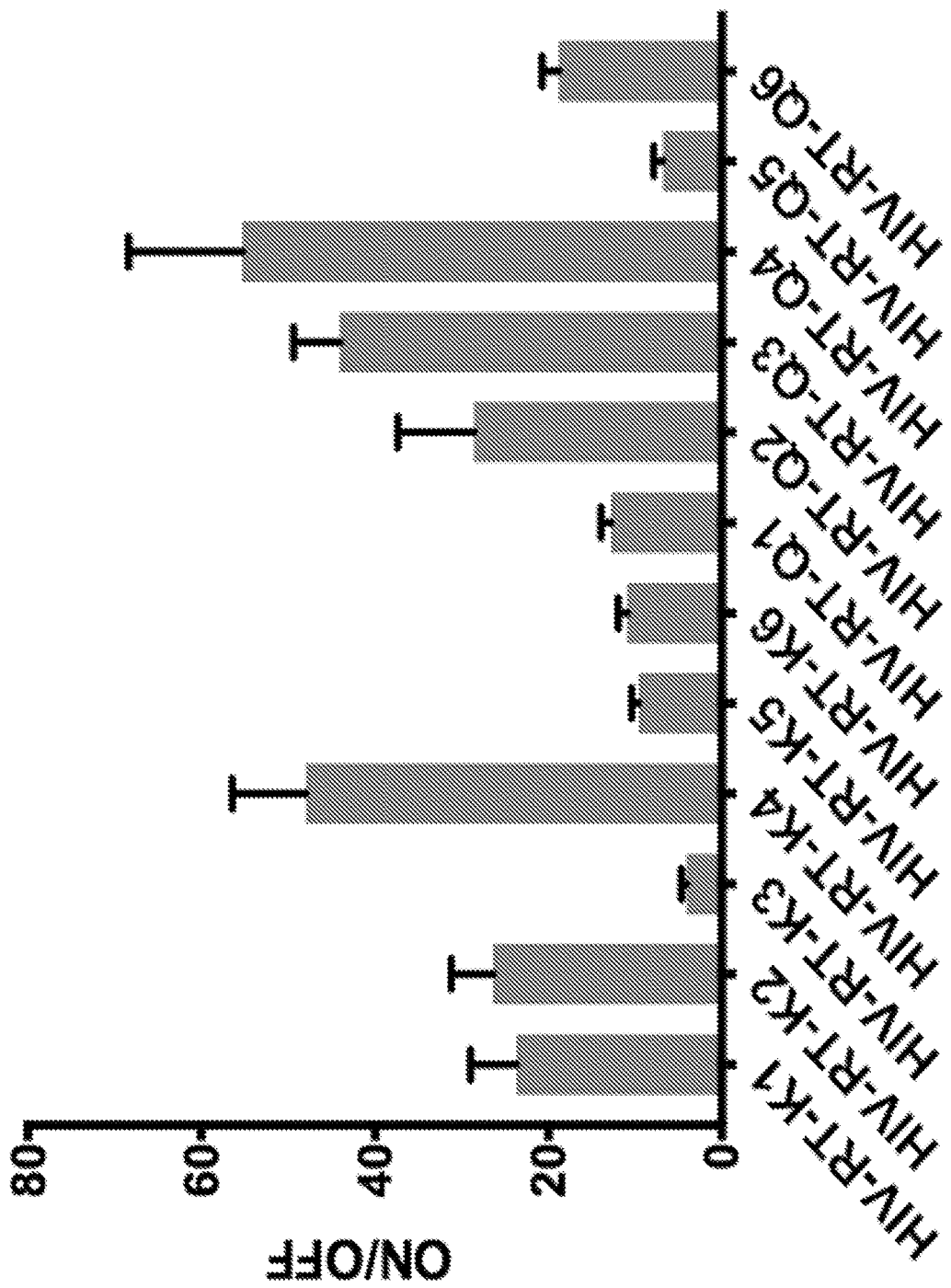
Figures 10A, 10B, 10C, 10D:
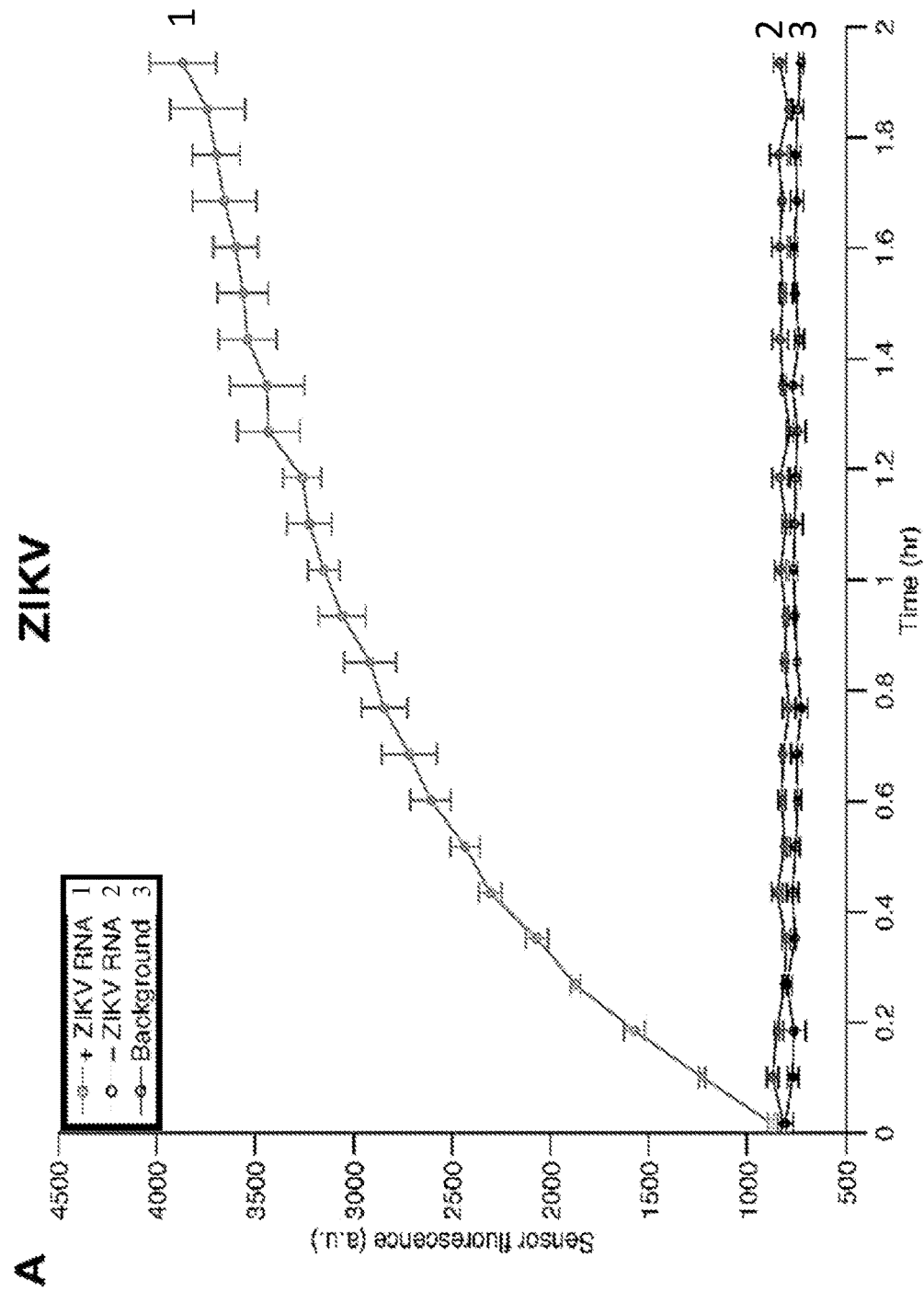
Figures 11A, 11B, 11C, 11D:
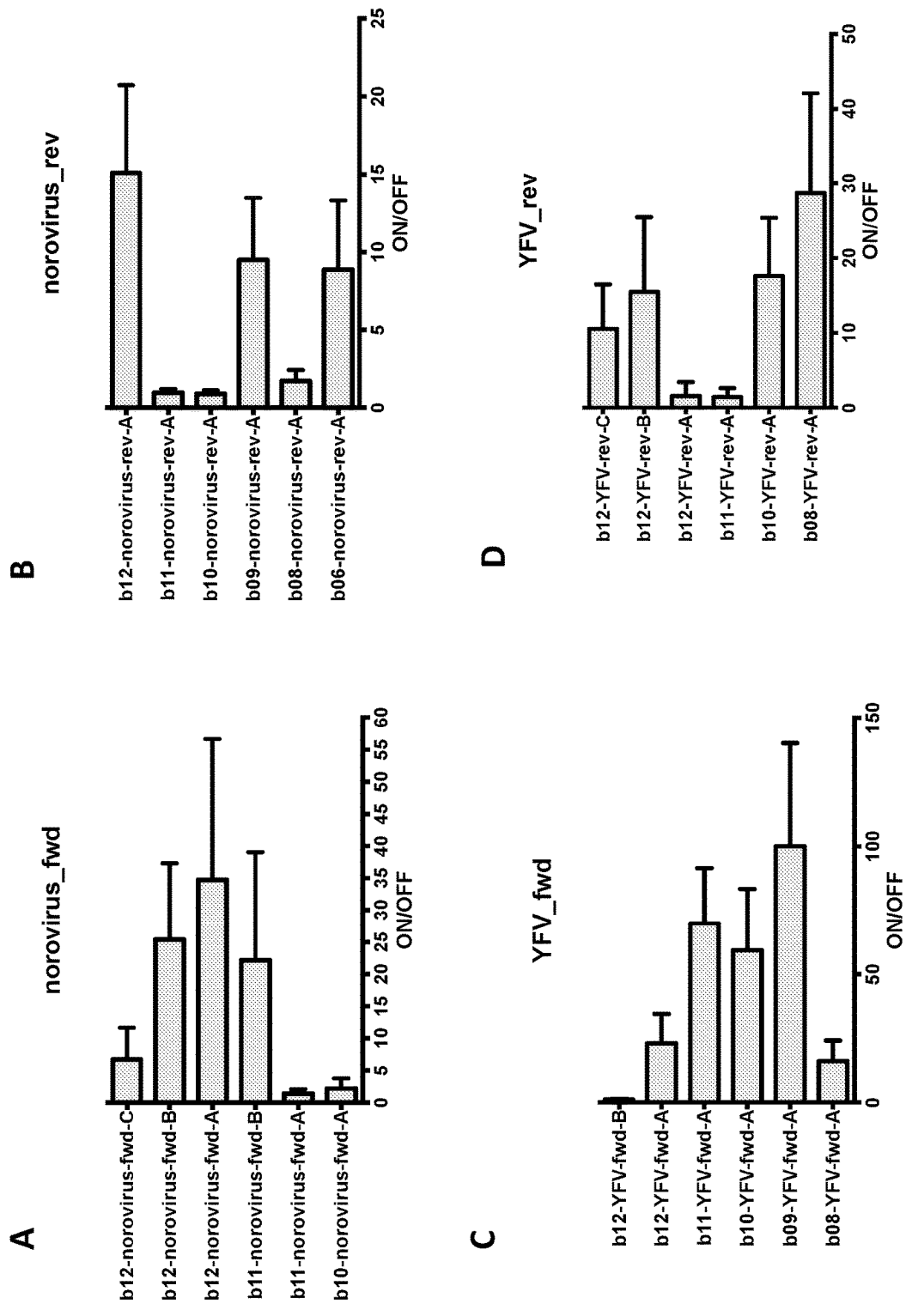

FIG. 9 is a graph showing detection of HIV RNA using Broccoli-based RNA sensors. The ON/OFF ratio of a series of Broccoli-based sensors targeted to the K65 (HIV-RT-K1 to 6) and Q151 (HIV-RT-Q1 to 6) residues of the HIV reverse transcriptase (HIV-RT) mRNA.

FIGS. 10A-10D demonstrate detection of multiple mosquito-borne viruses using Broccoli-based RNA sensors. Broccoli-based RNA sensors were designed for four different viruses transmitted by *A. aegypti*: (A) the Zika virus (ZIKV), (B) the chikungunya virus (CHIKV), (C) dengue virus serotype 1 (DENV1), and (D) dengue virus serotype 3 (DENV3). The fluorescence of sensors tested against their target RNAs is shown in lines labeled "1" while the fluorescence of the sensors in the absence of the target RNA is shown in lines labeled "2". The background fluorescence measured from the reaction buffer with DFHBI-1T is shown in lines labeled "3".

FIGS. 11A-11D are graphs showing detection of (A) target sense (fwd) RNAs from the norovirus genome, (B) target antisense (rev) RNAs from the norovirus genome, (C) target sense (fwd) RNAs of the yellow fever virus (YFV), and (D) target antisense (rev) RNA of the yellow fever virus (YFV) using Broccoli-based RNA sensors. Six sensors were designed for each target. ON/OFF ratios were obtained via plate reader measurements taken after 1 hour of target-sensor hybridization. Error bars are the standard deviation values from three replicates.

Figures 12A, 12B:
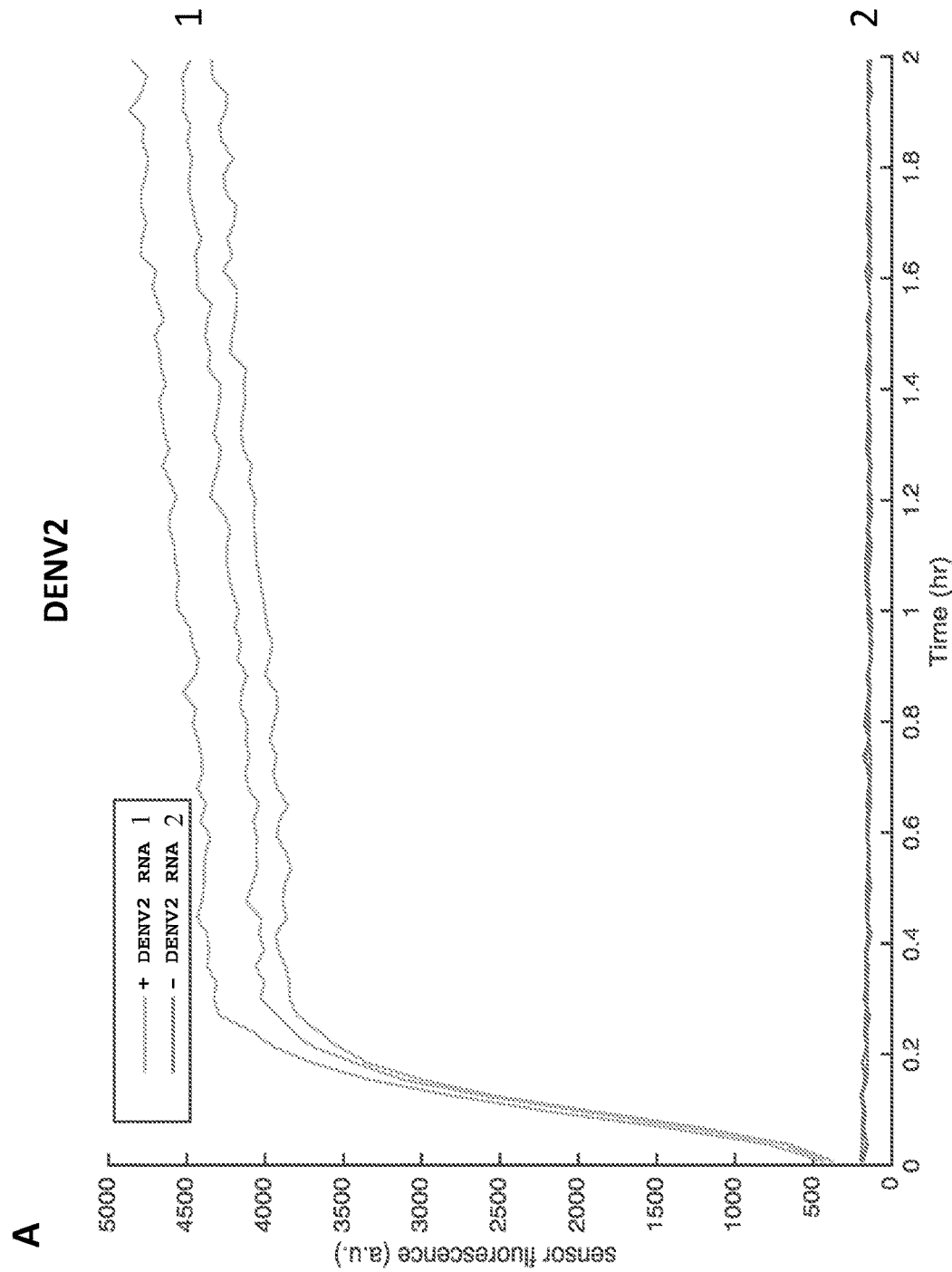

FIGS. 12A-12B demonstrate detection of dengue virus using Broccoli-based RNA sensors. Broccoli-based RNA sensors were designed for two different serotypes of dengue viruses: (A) dengue virus serotype 2 (DENV2), and (B) dengue virus serotype 4 (DENV4). The fluorescence of sensors tested against their target RNAs is shown in lines labeled "1" while the fluorescence of the sensors in the absence of the target RNA is shown in lines labeled "2".

Figure 13A:
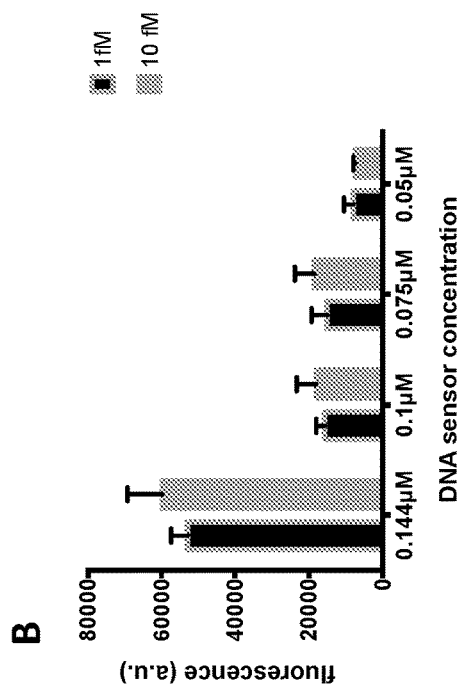
Figure 13B:
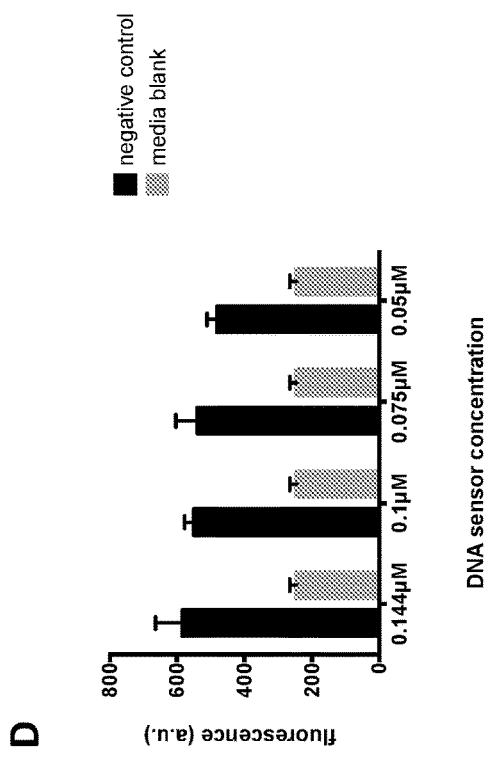

FIGS. 13A-13B demonstrate integration of Broccoli-based RNA sensors and RT-RPA-TX in one-pot reactions with Pfs25fwd sensor. (A) Fluorescence measurements were taken after 1-hour incubation of RT-RPA-TX product, 2 μM RNA sensor and DFHBI-1T buffer. RNA amplicons were diluted using 10 μg/ml transfer RNA. (B) Sample fluorescence intensities were taken after 2-hour one-pot reactions with 10 fM (gray bars) or 1 fM (black bars) of the target RNA and 0.144, 0.1, 0.075 or 0.05 μM of sensor DNA. (C) ON state (with 10 fM target RNA), negative control (with 10 fM non-target RNA amplicon) and media blank (DFHBI-1T buffer) fluorescence data for the RT-RPA-TX one-pot reactions. (D) Fluorescence data of negative control and media blank for the one-pot reactions showing low sensor output in the absence of the cognate target RNA. Error bars are the standard deviation values from three replicates.

Figures 14A, 14B, 14C:
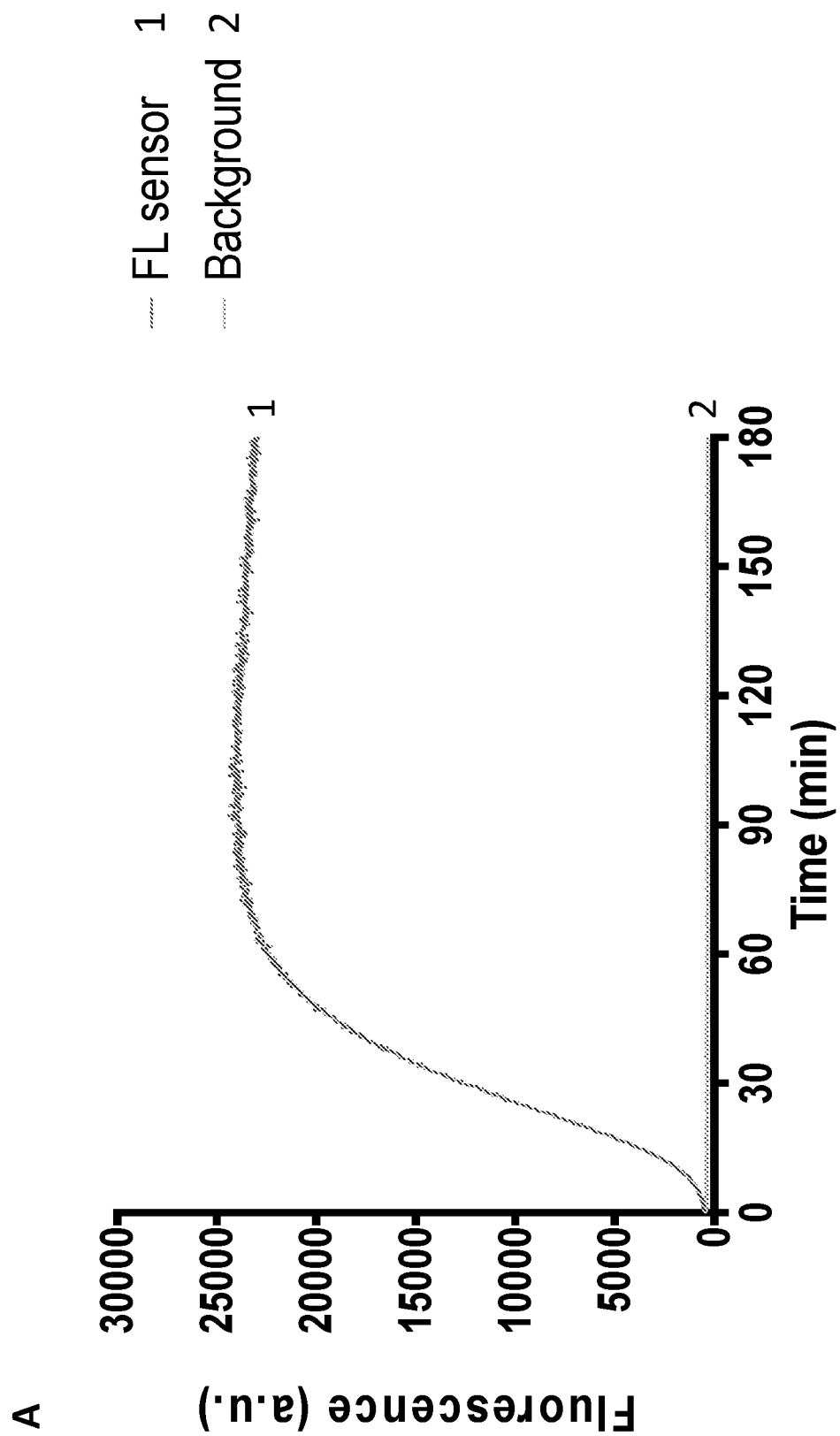

FIGS. 14A-14C are graphs showing the detection of LAMP products using Broccoli-based RNA sensors. Broccoli-based RNA sensors were designed for detection of malaria by detecting PfMt869 DNA of *Plasmodium falciparum*. The best two Broccoli sensors are (A) Forward loop (FL) sensor and (B) backward loop (BL) sensor which detect the loop regions of the LAMP products. (A, B) Show the fluorescence of the PfMt869 sensors upon detection of RNAs transcribed from the LAMP DNA products amplified to include T7 promoters. (C) Demonstration of the RNA Broccoli detecting both RNA (with pT7 primer) and DNA (without pT7 primer) LAMP products. The fluorescence of sensors tested against their target RNAs (with pT7 primer) is shown in lines labeled "1", the fluorescence of sensors tested against their target DNAs (without pT7 primer) is shown in lines labeled "3", and the fluorescence of the DFHBI-1T buffer in the absence of sensor RNA is shown in lines labeled "2". Fluorescence signals of the in vitro transcription of the Broccoli sensor and LAMP products were measured using plate reader for 3 hours.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and compositions provided herein are based at least in part on the inventors' development of an effective strategy for specific detection of pathogen nucleic acids—a strategy that employs inexpensive enzymatically produced sensors and a fluorescent readout that can be seen by eye. These detection systems employ unimolecular aptasensor designs that trigger the formation of functional aptamers in response to the binding of pathogen target nucleic acids (e.g., RNA, DNA) with arbitrary sequences.

Without being bound to any particular theory or mechanism of action, it is believed that the inventors addressed limitations in the practical deployment of nucleic acid based molecular diagnostics by combining isothermal amplification methods with unimolecular aptamer-based sensors ("aptasensors") that activate detectable, conditional fluorophores or color-emitting molecules, are capable of detecting a large diversity of target sequences, and have a dynamic range of fluorescence over 100-fold with low leakage. As described in the paragraphs and Examples that follow, the advantages of the aptasensors and methods provided herein are multifold and include, for example, transcription-only reactions that employ high dynamic range aptasensors and can be integrated with existing amplification methods for one-pot amplification/detection reactions. Moreover, the aptasensors and methods provide SNP-specificity, do not require translation systems, can detect arbitrary sequences, provide fluorescence and colorimetric readouts, and can provide single-base resolution with greatly reduced reaction times.

Accordingly, in a first aspect, provided herein are unimolecular aptamer-based sensors capable of binding to the target analyte. As used herein, the terms "aptamer-based sensor," "aptasensor," and "aptamer beacon" are used interchangeably to refer to a sensor (e.g., biomolecule sensor) that can be used to capture a target analyte by exploiting the affinity of an aptamer to its target and that can be detected using techniques identifiable by a skilled person upon reading of the present disclosure. The term "aptamer" as used herein refers to nucleic acids or peptide molecules that are capable to bind a specific target. In particular, aptamers can comprise single-stranded (ss) oligonucleotides and peptides, including chemically synthesized peptides. Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Although examples in this disclosure illustrate detection of RNA, it will be understood by those having ordinary skill in the art that the target analyte to be detected may be any nucleic acid including DNA. Accordingly, while RNA aptamers are exemplified, it will be understood that this disclosure encompasses analogous DNA aptamer-based sensors and DNA target analytes.

The base design of aptamer-based sensors described herein was inspired by the toehold switch, a recently developed riboregulator. As used herein, the term "toehold switch" generally refers to a regulator of gene expression, configured to repress or activate translation of an open reading frame and thus production of a protein. Referring to the example illustrated in FIG. 2A, the binding of a cognate trigger RNA to a toehold switch activates gene translation downstream. The RNA stem-loop structure located upstream of the repressed output gene is responsible for sensing of the target RNA. The ribosomal binding site (RBS) and start codon for the output gene are positioned within the loop and within a bulge on the stem, respectively. When the trigger RNA binds to the single-stranded region at the 5' end (toehold), the stem will gradually unwind, and the RBS and the start codon will be exposed. As a result, the translation of the output gene will be activated.

In certain embodiments, the unimolecular aptamer-based sensor comprises a synthetic nucleic acid molecule comprising (a) a fully or partially double-stranded stem-forming domain, (b) a toehold domain, (c) a loop-forming domain, and (d) an aptamer sequence, wherein at least a portion of the synthetic nucleic acid molecule is complementary to a target nucleic acid sequence. The aptamer sequence can be bound to at least one signal-generating ligand (e.g., a fluorophore). The signal-emitting ligand can generate a fluorescent signal or a colorimetric signal. In such cases, the sensor is configured for binding of the target nucleic acid sequence to the toehold domain and activation of fluorescence emission or production of a visible color in the presence of the target nucleic acid sequence. The sensor can be configured for binding of the target nucleic acid sequence to the toehold domain and formation of a guanine quadruplex in the presence of the target nucleic acid sequence.

In some cases, aptamer-based sensors described herein avoid the expression of a protein as the output by using a fluorophore aptamer as its output. Referring to the example illustrated in FIG. 2B, domain a is a 15-nt toehold region that initiates the interaction with the target RNA. It is followed by a 20-nt stem, 8-nt loop structure with two 1-nt bulges in the c/c* domains, where the "*" symbol denotes a complementary sequence. By way of example, a Broccoli aptamer core, which lacks the stabilizing stem, is positioned downstream of the nucleic acid sensing element. In this example, the adjacent b domains complete the Broccoli aptamer, and are responsible for stabilizing of the correct aptamer fold upon target RNA binding. In the absence of the target RNA, the aptamer-based sensor will not be stably folded as the b domain is sequestered within the stem, thus the system is non-fluorescent. In the presence of the target RNA, the b* domain will be released from the stem-loop structure of the sensor and it will hybridize with the downstream b domain. As a result, Broccoli aptamer is securely folded, and activates fluorescence of the bound fluorophore, (Z)-4-(3,5-difluoro-4-hydroxybenzylidene)-1,2-dimethyl-1H-imidazol-5(4H)-one (DFHBI).

Figures 2A, 2B:
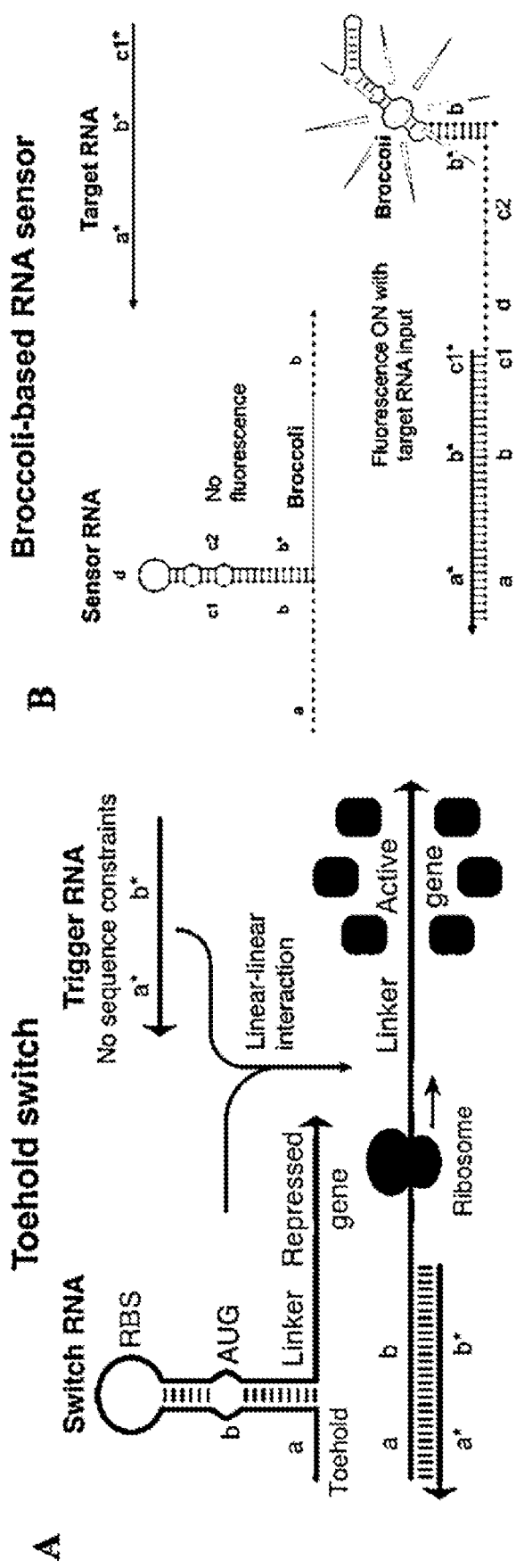
FIGS. 2A-2B are schematics illustrating exemplary designs of toehold switch and Broccoli-based sensors. (A) Toehold switch design: the target RNA or DNA binds to the toehold region of the switch to disrupt the repressing stem-loop and activate translation of the downstream gene. (B) An example Broccoli-based RNA sensor design: the target RNA binds to the toehold region of the sensor to unwind the stem-loop and activate the fluorescence of the Broccoli-DFHBI-1T complex.

In some cases, a unimolecular aptamer-based sensor of the present disclosure can form a hairpin structure comprising a stem domain and a loop domain through complementary base pairing, and further comprising an aptamer-fluorophore complex. In some embodiments, the stem domain of the hairpin structure can be as small as 4 bps, but in some cases will be longer than 4 bps, including 5, 6, 7, 8, 9, 10, 11, 12, or more base pairs in length. In some cases, the loop domain is complementary to a naturally occurring nucleic acid. In other cases, the loop domain is complementary to a non-naturally occurring nucleic acid. The toehold sequence domain can be 3, 4, 5, 6, 7, 8, 9, 10, 11, 12, 13, 14, 15, 16, 17, 18, 19, 20, or more nucleotides in length. Referring to FIG. 2B, the stem-forming domain can in some cases overlap with at least a portion of the aptamer sequence. In such cases, the sensor is configured for binding of the target nucleic acid sequence to the toehold domain and activation of fluorescence emission or production of a visible color in the presence of the target nucleic acid sequence.

In certain embodiments, any appropriate fluorescent aptamer can be used for aptamer-based sensors ("aptasensors") described herein. For example, the fluorescent RNA aptamer can be Broccoli. As used herein, the term "Broccoli" or "Broccoli aptamer" refers to a 49-nt fluorescent RNA aptamer-fluorophore complex (see Filonov et al., *J. Am. Chem. Soc.* 2014, 136(46):16299-16308) that confers fluorescence to a target analyte (e.g., target RNA) of interest via activation of the bound fluorophore DFHBI or a DFHBI-derived fluorophore such as (Z)-4-(3,5-difluoro-4-hydroxybenzylidene)-2-methyl-1-(2,2,2-trifluoroethyl)-1H-imidazol-5(4H)-one) (DFHBI-1T) as described by Song et al., *J. Am. Chem. Soc.* 2014, 136:1198. Other fluorescent RNA aptamers that can be used include, without limitation, Spinach and Spinach2 (Strack et al., *Nature Methods* 2013, 10:1219-1224), Carrot and Radish (Paige et al., *Science* 2011, 333:642-646), RT aptamer (Sato et al., *Angew. Chem. Int. Ed.* 2014, 54:1855-1858), hemin-binding G-quadruplex DNA and RNA aptamers, and malachite green binding aptamer (Babendure et al., *J. Am. Chem. Soc.* 2003). As will be understood by practitioners in the art, selection of a fluorescent RNA aptamer-fluorophore complex for use in an aptasensor described herein will depend on fundamental properties of the aptamer such as brightness (or enzymatic output), folding properties, and amenability to sequence modifications.

In other cases, any appropriate colorimetric aptamer can be used for aptamer-based sensors ("aptasensors") described herein. In such cases, the aptasensors are aptamer-based colorimetric sensors and the presence of a target nucleic acid is indicated by a color change occurring in response to the analyte. The term "colorimetric" is defined as an analysis where the reagent or reagents constituting the aptasensors system produce a color change in the presence or absence of an analyte. The degree the color changes in response to the analyte (e.g., target nucleic acid) may be quantified by colorimetric quantification methods known to those of ordinary skill in the art in. In some cases, standards containing known amounts of the selected analyte may be analyzed in addition to the sample to increase the accuracy of the comparison.

Figures 7A, 7B, 7C:
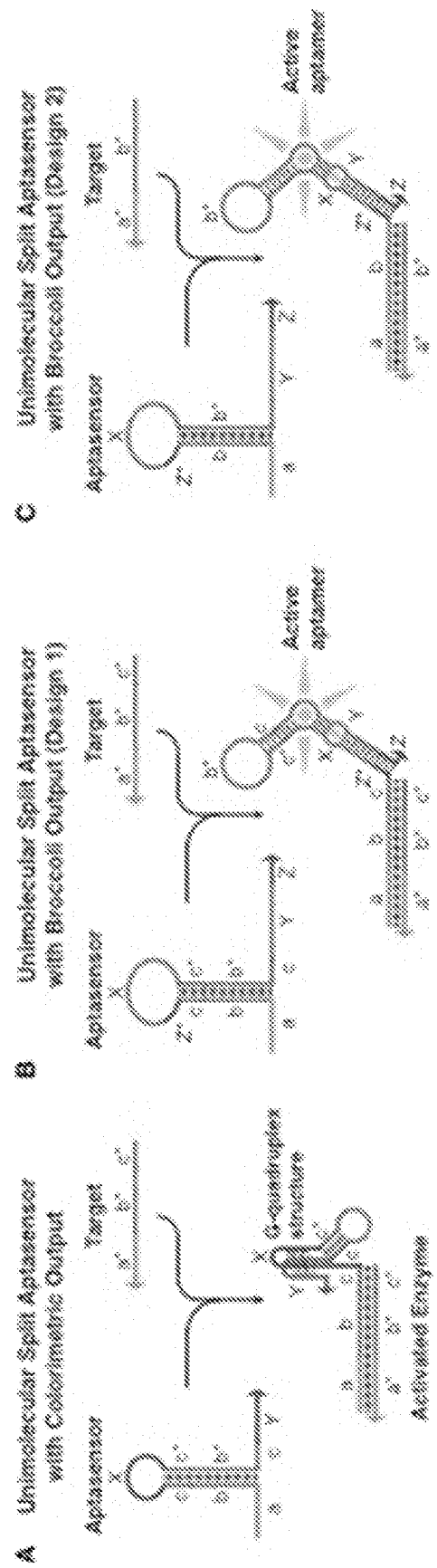
FIGS. 7A-7C present schematics of exemplary designs of unimolecular split aptasensors. (A) Colorimetric sensor design: the target RNA binds to the toehold region of the switch to disrupt the repressing stem-loop which allows formation of the G-quadruplex aptamer structure. Binding of hemin to the DNA aptamer produces a colorimetric readout upon catalysis by the DNA enzyme ("DNAzyme"). (B) Unimolecular split Broccoli sensor design 1: the target RNA binds to the toehold region of the sensor to unwind the stem-loop which allow the two parts of the Broccoli to come together and activate the fluorescence of the Broccoli-DFHBI-1T complex. (C) Unimolecular split Broccoli sensor design 2: This design is similar to design 1 (B), except that the aptasensor stem must be fully unwound before favorable interactions between X and Y halves of the aptamer occur.

In some cases, the aptamer sequence is split into at least two portions, whereby one portion of the aptamer sequence is located in the loop-forming domain, and a second portion of the aptamer sequence is downstream of the stem-forming domain. In another aspect, therefore, provided herein are unimolecular split aptamer-based sensor ("split aptasensor"). Referring to FIG. 7A, a unimolecular split aptamer-based sensor comprises one half of the desired aptamer positioned at the loop of the sensor (domain X, 'GGGTAGGG') and, thus, sequestered from the other half (domain Y, 'GGGTTGGG'). Upon binding of the target RNA, the stem-loop of the sensor will be gradually disrupted and the binding of the c* domain to the downstream c domain will bring into close proximity both halves of the split aptamer. Localization of the two halves promotes formation of the G-quadruplex structure and activates the DNA enzyme. For the colorimetric sensor designs, we varied the length of the c/c* domains (6, 7, and 8 nts) and employed 0-, 2-, or 3-nt spacers. While the aptamer exemplified in FIG. 7A is a DNA aptamer, this disclosure encompasses analogous RNA split aptamer-based sensors. For example, unimolecular RNA split aptamer-based sensors can be designed using a RNA version of the hemin-binding aptamer. In some cases, additional domains can be added upstream and downstream of the X and Y domains in the aptasensor. Such domains can be used to provide flexibility to the system to encourage the G-quadruplex to form. These domains can also be used to contribute additional bases for pairing to help stabilize the G-quadruplex, again encouraging it to form. For example, domains Z and Z* could be added to the G-quadruplex split aptasensor in FIG. 7A at the same locations with respect to X and Y domains as the split Broccoli-aptasensor design depicted in FIG. 7B. Upon activation of such a G-quadruplex aptasensor, the complementary Z and Z* will hybridize and encourage folding of X and Y into the desired G-quadruplex aptamer structure. The length of such Z and Z* domains can be 3, 4, 5, 6, 7, 8, or more nucleotides in length.

In some cases, unimolecular RNA split aptamer-based sensors are based on Broccoli aptamers. Referring to FIG. 7B, a standard or rotated Broccoli aptamer can be split into two halves: domain X=UCUGAGACGGUCGGGUC (SEQ ID NO:1) and domain Y=UCGAGUAGAGUGU-GGG-CUCAGA (SEQ ID NO:2) (FIG. 7B). In some cases, the length of the c/c* domains of unimolecular split Broccoli aptasensors can be varied. For example, an alternative Broccoli-based sensor is shown in FIG. 7C. In this split aptasensor, the b/b* extends the full length of the stem and there is no c domain in the system. Complete stem unwinding by the target RNA enables X and Y to bind to one another and with the assistance of the clamping domains Z/Z* form the active Broccoli aptamer.

It is expected that, for some applications, unimolecular split aptamer systems have several advantages as compared to the unimolecular aptasensor design shown in FIG. 2B. First, by sequestering one half of the aptamer within the loop, that half of the aptamer is much more inaccessible compared to sequestration of the b/b* domains used in the FIG. 2B design. Second, unimolecular split designs can support partial unwinding of the bottom of the sensor stem and still avoid system activation. In the designs in FIGS. 7A-7B, the aptamer stem up to at least the c/c* domain must be unwound in order to begin aptamer formation. In the FIG. 7C design, the full stem must be unwound before activation. This added stringency for activation leads to more sensitive thermodynamics and should decrease leakage. In particular, it is expected that such systems should be amenable to SNP-specific sensing schemes to produce SNP-specific aptasensors.

In another aspect, provided herein is a method of detecting a target analyte using a unimolecular aptamer-based sensor, where the method comprises detecting a target analyte in a biological sample obtained from a subject. As described herein, such a method comprises or consists essentially of (a) obtaining RNA from a biological sample obtained from a subject; (b) amplifying the RNA with forward and reverse primers; (c) contacting the amplified RNA to a unimolecular aptamer-based sensor, where the sensor comprises a conditional-fluorophore-binding aptamer sequence and one or more toehold sequence domains complementary to an endogenous RNA sequence. For such methods, the unimolecular aptamer-based sensor comprises canonical RNA (or DNA) bases. Moreover, the unimolecular aptamer-based sensor can be viewed as a fluorophore itself since the conditional-fluorophore-binding aptamer binds to a dye molecule to activate fluorescence, such that the RNA (or DNA) and dye constitute the complete fluorophore. Preferably, the contacting occurs under conditions that allow activation of the conditional-fluorophore-binding aptamer of the aptamer-based sensor in the presence of the endogenous nucleic acid but not in the absence of the endogenous nucleic acid. In this manner, the unimolecular aptamer-based sensor can detect, for example, a target sequence of the genome of the pathogen of interest. The method further comprises detecting the fluorescence as an indicator that the endogenous RNA is present in the RNA amplified from the biological sample of the subject.

In other cases, the method employs non-fluorophore based steps. For example, binding of an endogenous RNA can promote formation of a DNA enzyme ("DNAzyme") or ribozyme that acts on a substrate to produce a visible color. Such non-fluorophore based methods can involve, for example, hemin-binding guanine quadruplex (G-quadruplex) aptamers. Hemin is a porphyrin, a small molecule that binds to the G-quadruplex. FIG. 7A illustrates a unimolecular split aptasensor that produces colorimetric output.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

In some cases, the method further includes detecting pathogen-associated nucleic acids in a biological sample obtained from a subject, where identifying comprises: (i) amplifying nucleic acid obtained from the biological sample; (ii) contacting the amplified nucleic acid of (i) to a unimolecular aptamer-based sensor under conditions that allow for sequence-specific activation of the aptamer-based sensor when a pathogen-specific nucleic acid is present; and (iii) detecting activation of the aptamer-based sensor by detecting fluorescence of the bound fluorophore, where fluorescence is not detectable in the absence of the pathogen-specific target nucleic acid, thereby indicating the presence of the pathogen-specific nucleic acid.

The methods provided herein can detect virtually any pathogen for which genetic information (e.g., gene sequences) is available. By way of example, pathogens may comprise viruses including, without limitation, flaviviruses, human immunodeficiency virus (HIV), Ebola virus, single stranded RNA viruses, single stranded DNA viruses, double-stranded RNA viruses, double-stranded DNA viruses. Other pathogens include but are not limited to parasites (e.g., malaria parasites and other protozoan and metazoan pathogens (*Plasmodia* species, *Leishmania* species, *Schistosoma* species, *Trypanosoma* species)), bacteria (e.g., *Mycobacteria*, in particular, *M tuberculosis, Salmonella, Streptococci, E. coli, Staphylococci*), fungi (e.g., *Candida* species, *Aspergillus* species, *Pneumocystis jirovecii* and other *Pneumocystis* species), and prions. In some cases, the methods detect malaria infection by detecting Pfs25 mRNA of *Plasmodium falciparum* in a biological sample obtained from a subject. As described in the Examples, in some cases, the methods detect Pfs25 mRNA of *Plasmodium falciparum* at concentrations down to at least 1 fM and the fluorescent readout is detectable (e.g., visible to the aided or unaided human eye).

In certain embodiments, the methods detect viruses including, without limitation, the human-pathogenic flaviviruses such Zika virus (e.g., Zika strain from the Americas, ZIKV), yellow fever virus, and dengue virus serotypes 1 (DENV1) and 3 (DENV3), and closely related viruses such as the chikungunya virus (CHIKV). In other embodiments, the methods detect negative-stranded RNA viruses such as Ebola virus and positive-stranded RNA viruses, such as viruses of the family Caliciviridae (e.g., human enteric viruses such as norovirus and sapovirus). As described in the Examples, the methods in some cases employ Broccoli-based sensors to detect target nucleic acids derived from viral genomes. Specifically, the steps for detecting the presence of viral nucleic acids comprise isothermal amplification. In some cases, the isothermal amplification is NASBA (nucleic acid sequence-based amplification). The three enzymes involved in a NASBA reaction are a reverse transcriptase, RNase H, and T7 RNA polymerase. The amplification process begins with binding of the NASBA reverse primer to a target RNA, and an RNA/DNA duplex is created by reverse transcription. The RNA template is then degraded by RNase H which only targets RNA in RNA/DNA duplex, but not single-stranded RNA (target RNA). Now the single-stranded DNA is ready for the binding of the forward NASBA primer containing the T7 promoter for the elongation of the complementary strand. Finally, T7-mediated transcription of the double-stranded DNA templates creates copies of the target RNA sequence. Newly synthesized RNAs not only can be detected by the fluorescence-based RNA aptasensors described herein but also serve as the starting material for further RNA amplification cycles. To increase the yield of the RNA amplification reaction, inosine 5'-triphosphate is widely used to replace approximately 25% of the canonical rGTP. In some cases, a forward primer is used to introduce a T7 promoter site into the resulting DNA template to enable transcription of amplified RNA products via T7 RNA polymerase. In other cases, a reverse primer is used to add a trigger sequence of a toehold sequence domain.

Any isothermal amplification protocol can be used according to the methods provided herein. In some cases, isothermal amplification comprises NASBA (nucleic acid sequence-based amplification). Other isothermal amplification methods include: loop-mediated isothermal amplification (LAMP), strand displacement amplification (SDA), helicase-dependent amplification (HDA), nicking enzyme amplification reaction (NEAR), signal mediated amplification of RNA technology (SMART), rolling circle amplification (RCA), isothermal multiple displacement amplification (IMDA), single primer isothermal amplification (SPIA), recombinase polymerase amplification (RPA), and polymerase spiral reaction (PSR), which is described at nature.com/articles/srep12723 on the World Wide Web. In some cases, recombinase polymerase amplification (RPA) is used with the "one-pot" amplification and detection methods provided herein. In such cases, the methods comprise performing reverse transcription (RT), RPA, and transcription (TX) methods in a single test tube. In other cases, LAMP (loop-mediated isothermal amplification) is performed. As described in the Examples that follow, the unimolecular aptamer-based sensors described herein can bind directly to DNA LAMP amplification products. Alternatively, the amplification protocol is configured to add promoter sites to DNA LAMP amplification products such that each LAMP DNA can generate multiple RNA copies for improved assay effectiveness.

Nucleic acids and/or other moieties of the invention may be isolated. As used herein, "isolated" means to separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

As used herein, a "sample" means any material that contains, or potentially contains, which could be infected or contaminated by the presence of a pathogenic microorganism. Samples appropriate for use according to the methods provided herein include biological samples such as, for example, blood, plasma, serum, urine, saliva, tissues, cells, organs, organisms or portions thereof (e.g., mosquitoes, bacteria, plants or plant material), patient samples (e.g., feces or body fluids, such as urine, blood, or cerebrospinal fluid), food samples, drinking water, and agricultural products. In some cases, samples appropriate for use according to the methods provided herein are "non-biological" in whole or in part. Non-biological samples include, without limitation, plastic and packaging materials, paper, clothing fibers, and metal surfaces. In certain embodiments, the methods provided herein are used in food safety and food biosecurity applications, such as screening food products and materials used in food processing or packaging for the presence of pathogens in biological and/or non-biological samples. In other embodiments, the methods provided herein are used for anti-counterfeit applications, such as confirming that pharmaceuticals are genuine or confirming the identity of high value items that have been fabricated or are known to contain specific nucleic acid species.

In some cases, it may be advantageous to adapt the methods described herein for high-throughput, reproducible, and rapid detection, for example in a clinical setting. When aptasensor output is coupled to a reporter element, such fluorescence emission or a color-change through enzymatic activity, the aptasensors act as genetically encodable sensors and imaging probes for endogenous virus RNAs in a sample. For example, such aptasensors can be provided in a device configured for rapid, reproducible detection in a clinical setting. In some cases, the device comprises a preserved paper test article, upon which any step(s) of the method provided herein can be performed. In preferred embodiments, the paper test article is preserved by freeze-drying, the aptasensors and methods provided herein can be performed for clinical application at a cost of less than $1 per assay and do not require translation to produce reporters for the diagnostic test. In other embodiments, the enzymes and DNA encoding the aptasensors can be freeze-dried in test tubes to render them stable at room temperature. These freeze-dried components can be reactivated upon addition of a sample and water, and can report on the presence of an endogenous nucleic acid of interest in the sample.

In some cases, the device is used with a portable electronic reader. In this manner, the electronic reader serves as companion technology that provides robust and quantitative measurements of device outputs. An exemplary electronic reader comprises readily available consumer components, open-source code, and laser-cut acrylic housing, and is powered by a rechargeable lithium ion battery. The electronic reader can further comprise an onboard data storage unit. In some cases, to achieve sensitive detection of aptasensor signal output, an acrylic chip that holds the freeze-dried, paper-based reactions or test tube reactions is placed into the reader between an LED light source (e.g., 470 nm or 570 nm), electronic sensors, and one or more optical filters as necessary. Using onboard electronics, samples can be read at a rate of 29 reads per minute. Accordingly, the portable electronic reader provides low-noise measurements of changes associated with the reporter element including changes in light transmission due to enzyme-mediated color change or aptamer-mediated fluorescence. Portable electronic readers can also be used to detect optical changes in samples processed in test tubes.

Articles of Manufacture

In another aspect, the present invention provides articles of manufacture useful for detecting a pathogen or identifying a pathogen strain. In preferred embodiments, the article of manufacture is a kit for detecting a pathogen, where the kit comprises a plurality of preserved paper test or test tube test articles and an electronic optical reader. Optionally, a kit can further include instructions for performing the pathogen detection and/or strain identification methods provided herein.

In certain embodiments, provided herein are paper-based or test tube-based articles of manufacture comprising freeze-dried or lyophilized amplification reagents and DFHBI-1T buffer components. For such embodiments, the paper-based or test tube-based articles of manufacture provide one-pot reactions that simply require rehydration for use as low-cost diagnostic tests that are appropriate for use in the field as well as in clinical settings. In certain of these embodiments, the paper-based or test tube-based articles of manufacture are provided with instructions for rehydrating the amplification and buffer components for use of the materials as diagnostic tests.

Unless defined otherwise, all technical and scientific terms used herein have the same meaning as commonly understood by one of ordinary skill in the art to which the invention pertains. All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein, "about" means within 5% of a stated concentration range or within 5% of a stated time frame.

It should also be understood that, unless clearly indicated to the contrary, in any methods claimed herein that include more than one step or act, the order of the steps or acts of the method is not necessarily limited to the order in which the steps or acts of the method are recited.

Having now described the invention, the same will be illustrated with reference to certain examples, which are included herein for illustration purposes only, and which are not intended to be limiting of the invention.

EXAMPLES

Reference is now made to the following examples, which together with the above descriptions illustrate the invention in a non-limiting fashion.

Example 1

Unimolecular Aptamer-Based Sensors for Detection of Pathogen RNAs in One-Pot Isothermal Reactions Materials and Methods Sensor DNA Template Preparation: All DNA oligonucleotides were designed using the NUPACK software package and custom Matlab scripts and purchased from Integrated DNA Technologies. DNA fragments were assembled and amplified via PCR.

RNA Synthesis: For in vitro transcriptions, AmpliScribe™ T7-Flash Transcription Kit (Epicenter) was used according to the manufacturer's instructions. Approximately 0.1 µM of concentration of each DNA template was added into each individual transcription reaction. For quantified of RNAs, DNase I was used to remove DNA template for the termination of the transcription, then RNA Clean & Concentrator™ (Zymo Research) was used for further purification.

NASBA: Reaction Buffer (Life Sciences; 33.5%), Nucleotide Mix (Life Sciences; 16.5%), RNase inhibitor (Roche; 0.5%), 12.5 mM of each NASBA primer (2%), nuclease free water (7.5%), and target RNA (5%) and 0.2 µM sensor DNA template (5%) were mixed at 4° C. and activated at 65° C. for 2 minutes, followed by a 10 min incubation at 41° C. Enzyme Mix (Life Sciences; 25%) and 80 µM DFHBI-1T buffer (5%) were then added to the reaction for a final volume of 5 µL. After mixing, the reaction was incubated at 41° C. for 2 hours.

Plate Reader Measurements: BioTek Synergy H1 Multi-Mode Reader was used for all plate reader measurements. 96-and 384-well plates were used for sensor screening and small-scale measurements, respectively. Before each measurement, samples were shaken linearly for 30 seconds to ensure proper mixing. The plate reader was preheated, and the measurements were all taken at 37° C.

RT-RPA-TX/Broccoli-based sensor one pot reaction: A single 50 µL reaction consisted of 1 tube of lyophilized RPA enzyme mix (TwistDX), lx RPA rehydration buffer, 0.48 µM of each forward and reverse primer, 4 µL Protector RNase inhibitor (Roche), 2 mM of each rNTPs (ATP, GTP, UTP, and CTP), 1 µL of AmpliScribe™ T7-Flash™ Enzyme Solution (Lucigen), varying concentrations of sensor DNA and target RNA amplicon, 4 µM of DFHBI-1T, 14 mM magnesium acetate. Reactions were incubated at 37° C. for 2 hours before fluorescence measurements.

Loop-mediated isothermal amplification (LAMP): The amplification reactions were performed according to the manufacturer's instructions for Bst 2.0 DNA Polymerase (New England Biolabs). Briefly, a 5 µL single reaction consisted of lx Isothermal Amplification Buffer II (NEB), 6 mM of $MgSO_4$, 1.4 mM of each dNTP, 1.6 µM of FIP/BIP primers, 0.2 µM of F3/B3 primers, 0.4 µM of LF/LB primers 320 U/mL of Bst 2.0 DNA Polymerase, synthetic target DNA templates, and water. After mixing, the reaction was incubated at 65° C. for 30 minutes. To add the T7 promoter sequence, 2 µM of the pT7_F2/pT7_B2 primers were added to the reaction mix. The reactions were allowed to proceed for another 10 minutes at 65° C. 0.5 µL LAMP products were then put into a 5 µL in vitro transcription reaction along with 0.2 uM Broccoli-based sensor DNA and 4 µM of DFHBI-1T. The transcription reaction was measured within a 384-well plate using a plate reader at 37° C. for 3 hours.

Results

Figure 1:
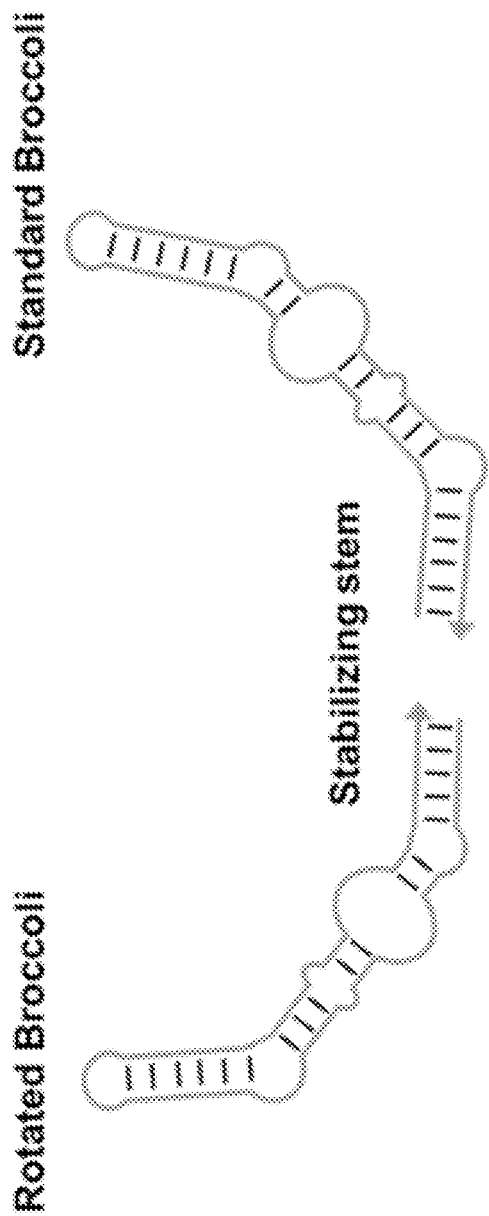
FIG. 1 illustrates secondary structures of two cyclic permutations of a Broccoli aptamer. (Left) Rotated Broccoli and (right) standard Broccoli.

Broccoli-Based Sensor Design: The secondary structures of the Broccoli aptamers are shown in FIG. 1. We termed the broccoli unit on the right side "standard" Broccoli (UCUGAGACGGUCGGGUCCA-GAUAUUCGUAUCU-GUCGAGUAGAGUGUGGGCUCAGA) (SEQ ID NO:3), as it is in the configuration first reported by Filonov et al. We termed the broccoli unit on the left side "rotated" Broccoli (UAUCUGUCGAGUAGAGUGUGGG-CUCAGAUUCGU-CUGAGACGGUCGGGU-CCAGAUA) (SEQ ID NO:4), as it is a circular permutation of the original aptamer. The stem at the terminals is essential to ensure proper folding of both aptamers.

The base design of our Broccoli-based RNA sensor is inspired by the toehold switch (FIG. 2A), a recently developed riboregulator. See Green et al., Cell, 159(4), 925-939 (2014). The binding of a cognate trigger RNA activates gene translation downstream. The RNA stem-loop structure located upstream of the repressed output gene is responsible for sensing of the target RNA. The ribosomal binding site (RBS) and start codon for the output gene are positioned within the loop and within a bulge on the stem, respectively. When the trigger RNA binds to the single-stranded region at the 5' end (toehold), the stem will gradually unwind, and the RBS and the start codon will be exposed. As a result, the translation of the output gene will be activated.

The Broccoli-based RNA sensor avoids the expression of a protein as the output by using the Broccoli aptamer as its output. As shown in the FIG. 2B, domain a is a 15-nt toehold region that initiates the interaction with the target RNA. It is followed by a 20-nt stem, 8-nt loop structure with two 1-nt bulges in the c/c* domains, where the "*" symbol denotes a complementary sequence. The Broccoli aptamer core, which lacks the stabilizing stem, is positioned downstream of the RNA sensing element. The adjacent b domains complete the broccoli aptamer, and are responsible for stabilizing of the correct aptamer fold upon target RNA binding. In absence of the target RNA, Broccoli-based RNA sensor will not be stably folded as the b domain is sequestered within the stem, thus the system is non-fluorescent. In the presence of the target RNA, the b* domain will be released from the stem-loop structure of the sensor and it will hybridize with the downstream b domain. As a result, the Broccoli aptamer is securely folded, and activates the fluorescence of the fluorophore DFHBI-1T.

Initial evaluation of Broccoli-based RNA sensors with conserved sequences: For our initial designs, we tested the Broccoli aptamer (rotated and standard versions) in sensors that retained the complete aptamer sequences originally reported by Filonov et al. (J. Am. Chem. Soc. 2014, 136 (46):16299-308). Thus, the b/b* domains of the sensors have sequences determined from the original Broccoli aptamer, while the rest of the domains have arbitrary sequences. We used the NUPACK software package for generation of the designs and picked the top two constructs (the ones with lowest ensemble defect scores) for each design, resulting in a total of 4 constructs. AmpliScribe™ T7-Flash Transcription Kit was used to transcribe both target and sensor RNAs. PCR was used to assemble and amplify the DNA fragments for the RNAs. DNAs are purified and quantified using Nanodrop after PCR. After transcription, RNAs are treated with DNase I for the removal of the DNA templates.

Approximately 0.5 µM of sensor RNA was mixed with excess amount (>5 fold) of the target RNA, along with 20 µM of DFHBI-1T buffer (40 mM HEPES pH 7.4, 100 mM KCl, and 1 mM $MgCl_2$). A plate reader (ex=472 nm, em=507 nm) was used to measure the fluorescence output of each combination of sensor and target RNA at 37° C. The ON state refers to the sensor RNA with its cognate target RNA, while the OFF state refers to the sensor RNA alone, in absence of any target RNAs. The autofluorescence of the 20 μM of DFHBI-1T buffer was also measured. The ON/OFF ratios from the mean fluorescence for our first 4 Broccoli-based RNA sensors are shown in FIG. 3A. The sensor with rotated Broccoli (rot.con.N2) provides an ON/OFF ratio exceeding 125-fold. FIG. 3B shows the fluorescence measured in the ON and OFF states for these aptasensors with the conserved aptamer sequences. The fluorescence measurements clearly show the low OFF state fluorescence from the systems and the clear increases in fluorescence upon activation, particularly for devices rot.con.N2 and sta.con.N2. These measurements thus confirm that the Broccoli-based sensing mechanism can be employed to trigger fluorescence upon target RNA binding.

Determining the effect of sequence changes to Broccoli fluorescent output: For successful use in nucleic acid tests, it is important to have an aptamer stem that is insensitive to changes in its sequence so that arbitrary target RNAs can be detected. Thus, we made changes to the stem sequences of both standard and rotated forms of Broccoli, and measured fluorescence intensities of the resulting Broccoli-DFHBI-1T complexes. We tested 8 stem variants for both standard and rotated Broccoli aptamers. Although standard Broccoli aptamers provide overall higher fluorescence, rotated Broccoli aptamers are less sensitive to changes in stem sequence, which suggests more reliable integration with sensors for detection of arbitrary target RNAs (FIG. 3C). In addition, the standard Broccoli aptamers possess a slightly longer stem than the rotated broccoli aptamers, which likely improved folding and increased their fluorescence compared to the rotated variants.

Since the OFF state signals for all four initial sensors were similar (~500 a.u.), the variations in their ON state signals caused the sizeable differences in their ON/OFF ratios. To increase the ON state signal, we increased the length of b domain (from 6 to 12 nts with 2-nt increments) to make the sensor-DFHBI-1T complex more stable. We also tested sensors with arbitrary b domains for both versions of Broccoli aptamers. Out of the 32 Broccoli-based RNA sensors, half of the sensors exhibited ON/OFF ratios over 20, and 5 provided ON/OFF ratios over 100 (FIG. 3D). Rotated Broccoli-based RNA sensors gave overall higher ON/OFF ratios. The sensors with stem length greater than 8-nt had higher leakage (higher OFF state signal) when compared to the ones with shorter stems, since longer stems might encourage the formation of the active Broccoli in the absence of the target RNAs. These results demonstrate the use of Broccoli-based sensors for detecting arbitrary RNAs can provide performance as good or better than those employing the conserved aptamer sequences.

Screening Broccoli-based RNA Sensors for Detection of *Plasmodium falciparum* RNA: Malaria remains one of the top ten causes of death in low income countries according to World Health Organization. It killed roughly 1200 people per day in 2015, most of whom are children under the age of five in African regions. *Plasmodium falciparum* is responsible for almost all of the malaria-attributed deaths. Asexual *Plasmodium falciparum* parasites inside humans cause clinical symptoms of malaria; whereas the presence of mature sexual stage parasites (gametocytes) are essential for the transmission of the disease from humans back to the mosquito and subsequent infection of humans. Therefore, early detection of gametocytes is critical for the containment and eradication of the disease. Current detection methods for malaria include microscopic diagnosis and molecular diagnosis (nucleic acid based detection). Microscopic diagnosis is the gold standard assay, but it has insufficient sensitivity at low gametocyte density in the blood. Molecular diagnosis including PCR and quantitative Nucleic Acid Sequence-Based Amplification (QT-NASBA) provide more accurate detection. However, these methods require well-trained technicians and well-equipped facilities not suitable for low-resource settings.

Figures 4A, 4B, 4C, 4D, 4E:
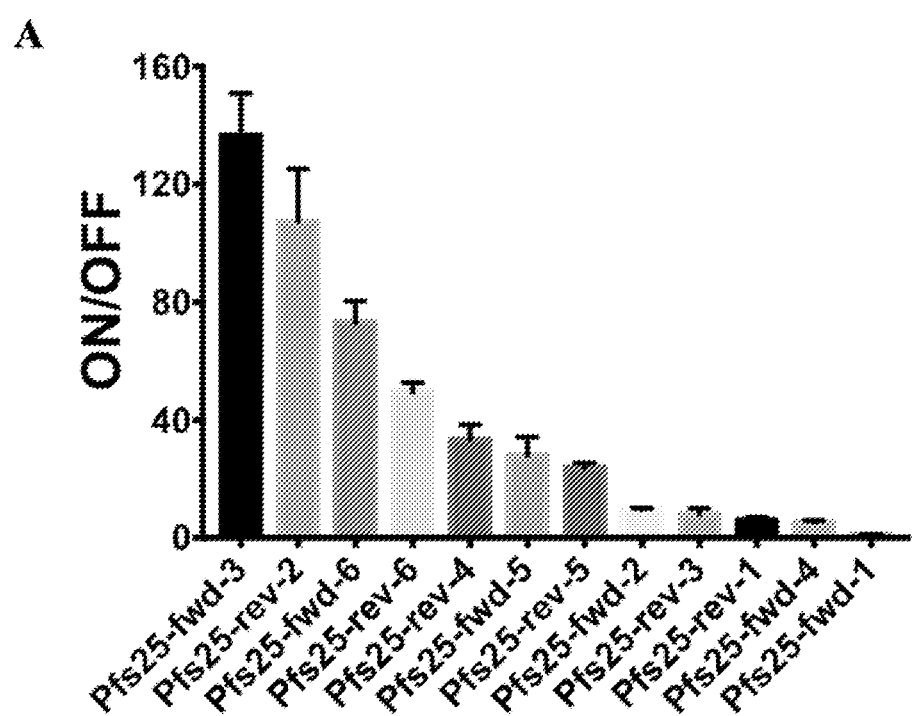
FIGS. 4A-4E present fluorescence data for Broccoli-based RNA sensors. (A) ON/OFF ratios of mean fluorescence for Broccoli-based RNA sensors detecting Pfs25 mRNAs. (B) Raw fluorescence data for Broccoli-based RNA sensor Pfs25-fwd-3. (C) Fluorescence data for Broccoli-based RNA sensor Pfs25-rev-2. (B,C) Each construct was measured in triplicate. Lines labeled "1" indicate the ON state, lines labeled "2" denote the OFF state, and lines labeled "3" mark the buffer background fluorescence. (D) and (E) Mean fluorescence data for Broccoli-based RNA sensor Pfs25-fwd-3 and Pfs25-rev-2 on a logarithmic fluorescence scale. Error bars are the standard deviation values from three replicates.

In view of these limitations, we designed Broccoli-based RNA sensors that detect the presence of gametocytes in *Plasmodium Falciparum*. Pfs25 mRNA is strictly expressed in late stage gametocytes, which are responsible for human-to-mosquito transmission of infection. Specifically, we generated Broccoli-based RNA sensors that target both sense (Pfs25 forward) and antisense (Pfs25 reverse) RNAs produced upon amplification of Pfs25 via NASBA using a custom sensor design algorithm. Briefly, we designed Broccoli-based RNA sensors that hybridized to a target RNA amplicon at 1-nt increments. This sliding window covers the internal region of the target RNA, leaving the outer portion for the binding of the NASBA primers to be used for amplifying the target RNA. The resulting Broccoli-based RNA sensors were analyzed for secondary structure, toehold availability, target-aptasensor binding probability, and the likelihood of forming the correct Broccoli aptamer structure following target binding. We only used the rotated version of Broccoli, and set the b domain length to 6, 7, and 8-nt, based on the findings reported in FIG. 3D. Top 6 constructs with the best predicted performance for sense and anti-sense Pfs25 RNAs were examined. In vitro tests were measured using a plate reader over 6 hours. After 1 hour of incubation at 37° C., 7 out of the 12 Broccoli-based RNA sensors provide ON/OFF ratios over 20. Out of those, three exhibited ON/OFF ratios over 100 (FIG. 4A). The best Broccoli-based RNA sensor for each target (Pfs25-fwd-3 and Pfs25-rev-2) was picked for subsequent measurements (FIGS. 4B-4C). Compared with the DFHBI-1T buffer autofluorescence, the OFF state fluorescent signal showed only a slight increase, which indicates the best Broccoli-based RNA sensors have very low leakage (<2 fold over background) as seen in the logarithmic scale plots in FIGS. 4D-4E.

Integrating Broccoli-based RNA sensors and NASBA in one pot reactions: Next we incorporated the isothermal RNA amplification technique NASBA. The three enzymes involved in the NASBA reaction are a reverse transcriptase, RNase H, and T7 RNA polymerase. The amplification process begins with binding of the NASBA reverse primer to the target RNA, and an RNA/DNA duplex is created by reverse transcription. The RNA template is then degraded by RNase H, which only targets RNA in RNA/DNA duplex, but not single-stranded RNA (target RNA). Now the single-stranded DNA is ready for the binding of the forward NASBA primer containing the T7 promoter for the elongation of the complementary strand. Finally, T7-mediated transcription of the double-stranded DNA templates creates copies of the target RNA sequence. Newly synthesized RNAs not only can be detected by the Broccoli-based RNA sensors, but also serve as the starting material for further RNA amplification cycles. To increase the yield of the RNA amplification reaction, inosine 5'-triphosphate is widely used for replacing approximately 25% of the canonical rGTP.

Figure 5:
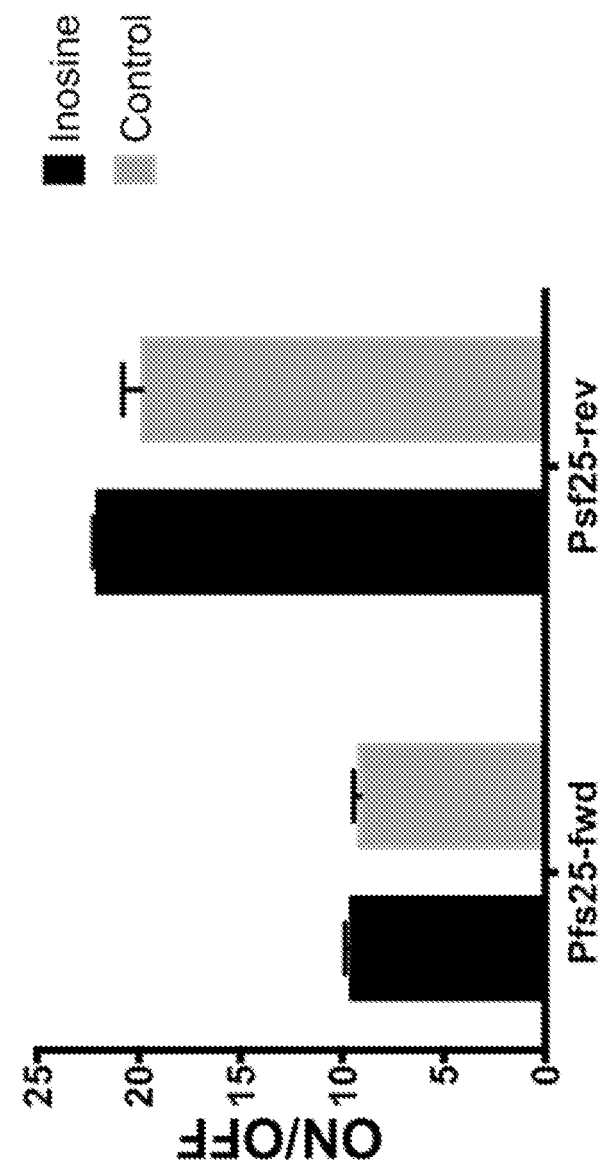
FIG. 5 presents ON/OFF ratios from the mean fluorescence for Pfs25 RNA targeting Broccoli-based RNA sensors. Plate reader measurements were taken after 1 hour of target-sensor hybridization. Error bars are the standard deviation values from three replicates. Controls were target RNA with regular rNTPs without inosine bases.

We first tested the NASBA kit for transcription of the standard Broccoli with stem variation (standard.var3.N1), and confirmed that Broccoli can still fluoresce with the incorporation of inosine bases. Then we transcribed our best two Pfs25 RNA targeting sensors using T7 transcription with same rNTP and rITP concentrations as the ones in NASBA reactions. For the ON state, we mixed approximately 1 µM sensor RNA with 1 µM target RNA at a total reaction volume of 10 µL; while for the OFF state we had approximately 1 µM sensor RNA with DFHBI-1T buffer alone. Broccoli-based RNA sensors with inosine bases provide the same fluorescence ON/OFF ratios as those obtained from RNAs with only canonical bases (FIG. 5).

Figure 6:
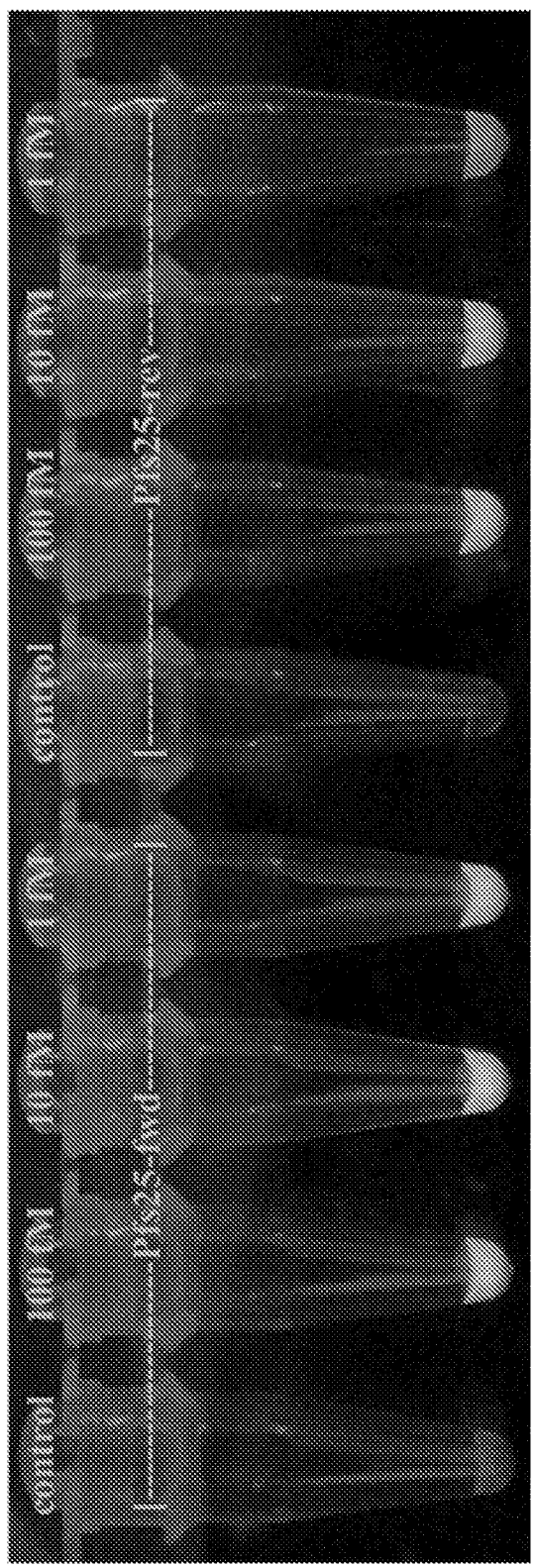
FIG. 6 demonstrates an application of broccoli-based RNA sensors to the detection of Pfs25 RNA in one-pot amplification/detection reactions. Pfs25 fwd (sense) and Pfs25 rev (anti-sense) RNA amplicons were added at input concentrations denoted at the top of the figure. Control samples had no target RNAs. The sample strip was photographed under blue light illumination after a 2-hour incubation at 41° C.

To apply the Broccoli-based RNA sensors to the detection of NASBA amplicon, we mixed 0.01 µM of the sensor DNA template with NASBA reaction components (specified in Materials and Methods) with target RNA concentrations of 100 fM, 10 fM, and 1 fM, and used a target-RNA-free reaction as the negative control. 4 µM of DFHBI-1T buffer and enzyme cocktail were added before a 2-hour isothermal incubation at 41° C. FIG. 6 shows a photograph of the resulting samples excited under a blue-light transilluminator using a blue-light filter to remove excess excitation light. The one-pot NASBA/Broccoli-based sensor reactions enable facile detection of Pfs25 RNA by eye down to at least 1 fM concentrations.

New Unimolecular Sensor Designs Based on Split Aptamer Systems: Although fluorescence-based detection is widely used for nucleic acid diagnostics, in many cases it is desirable to have simpler, colorimetric readout mechanisms that a patient or practitioner can easily observe by eye at the point of care. We have recently designed a new type of unimolecular probe that can provide colorimetric detection based on hemin-binding DNA and RNA aptamers with peroxidase activity[5]. A previous study has shown that the DNA aptamer can be used in a bimolecular probe system to enable colorimetric detection of DNA. This probe system employed two chemically modified DNA strands, each with half the sequence of the hemin-binding aptamer, along with two recognition domains for the desired target RNA. Upon binding to the target RNA, both halves of the DNA aptamer are brought into close proximity, enabling the full aptamer to reform. The DNA enzyme forms a guanine quadruplex structure in the presence of hemin and demonstrates peroxidase-like activity which causes a color change in the solution. This bimolecular probe, however, suffered from poor dynamic range due to spontaneous formation of the active aptamer in the absence of target and difficulties in forming a trimolecular DNA complex and required triethylene glycol linkers for successful function.

In our unimolecular split aptasensor design, we position one half of the desired aptamer at the loop of the sensor (domain X, 'GGGTAGGG') and sequester it from the other half (domain Y, 'GGGTTGGG') as shown in FIG. 7A. Upon binding of the target RNA, the stem-loop of the sensor will be gradually disrupted and the binding of the c* domain to the downstream c domain will bring into close proximity both halves of the DNA aptamer. Localization of the two halves promotes formation of a hemin-binding guanine-quadruplex (G-quadruplex) structure and activates the DNA enzyme. For the colorimetric sensor designs, we varied the length of the c/c* domains (6, 7, and 8 nts) and employed 0-, 2-, or 3-nt spacers. Analogous RNA-based designs were generated for the RNA version of the hemin-binding aptamer. Also note that additional domains can be added upstream and downstream of the X and Y domains in the aptasensor. Such domains can be used to provide flexibility to the system to encourage the G-quadruplex to form. These domains can also be used to contribute additional bases for pairing to help stabilize the G-quadruplex, again encouraging it to form.

We also designed Broccoli-based sensors employing this concept. We split the rotated Broccoli in half, having domain X=UCUGAGACGGUCGGGUC (SEQ ID NO:1) and domain Y=UCGAGUAGAGUGU-GGGCUCAGA (SEQ ID NO:2) (FIG. 7B), and removing 4-nt at the terminal loop 'UUCG'. To compensate for this 4-nt removal, we inserted Z and Z* domains for better stabilization of the active Broccoli upon hybridization to the target RNA. We have also varied the length of the c/c* domains of our unimolecular split Broccoli aptasensors. An alternative Broccoli-based sensor (Design 2, FIG. 7C) has a very similar design but with critical changes. In this aptasensor, the b/b* extends the full length of the stem and there is no c domain in the system. Complete stem unwinding by the target RNA enables X and Y to bind to one another and with the assistance of the clamping domains Z/Z* form the active Broccoli aptamer.

We expect such unimolecular split aptamer systems to have several advantages compared to the unimolecular aptasensor design shown in FIG. 2B. First, by sequestering one half of the aptamer within the loop, that half of the aptamer is much more inaccessible compared to sequestration of the b/b* domains used in the FIG. 2B design. Second, unimolecular split designs can support partial unwinding of the bottom of the sensor stem and still avoid system activation. In the designs in FIGS. 7A-7B, the aptamer stem up to at least the c/c* domain must be unwound in order to begin aptamer formation. In the FIG. 7C design, the full stem must be unwound before activation. This added stringency for activation leads to more sensitive thermodynamics and should decrease leakage. In particular, we expect that such systems should be amenable to SNP-specific sensing schemes such as those that we have previously employed for producing SNP-specific riboregulators.

Figures 8A, 8B:
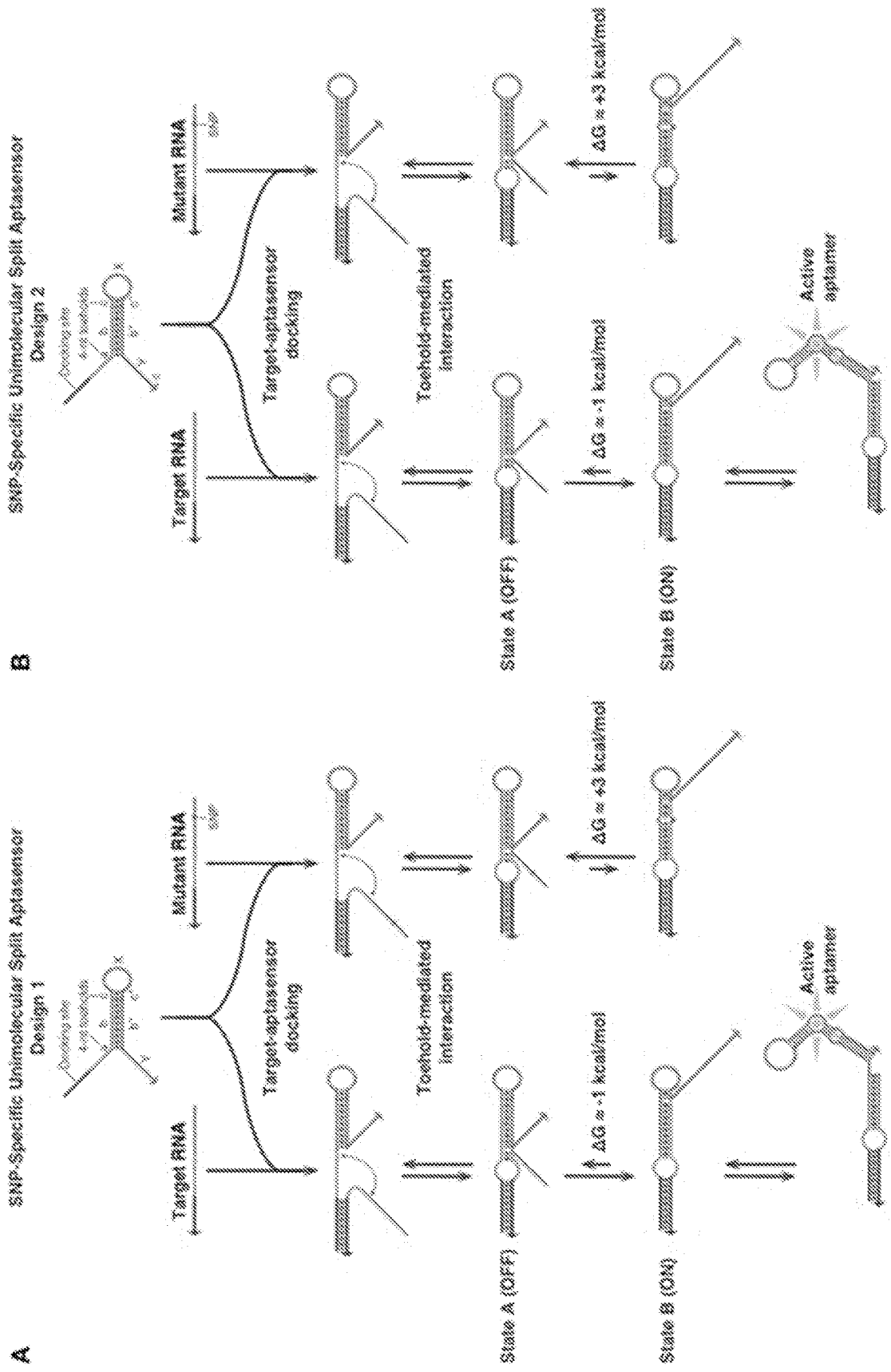
FIGS. 8A-8B present schematics of exemplary designs of unimolecular split aptasensors with SNP specificity. (A)

FIGS. 8A-8B provide two examples of such SNP-specific aptasensor designs. Both systems employ an extended docking site to promote strong binding of the target RNA to the aptasensor. Once this binding occurs, the target-aptasensor complex becomes a quasi-unimolecular system and thus enables subsequent interactions between the two RNAs to become effectively intramolecular and more sensitive to small changes in thermodynamics. In particular, a short, ~4-nt toehold domain is used to initiate a strand displacement process between the aptasensor and the target to unwind the repressing stem. Once this process occurs, the short toehold domain (domain c) is sufficiently short (~4-nts) to open transiently, enabling the active aptamer to form. Importantly, the thermodynamics of these quasi-intramolecular interactions are balanced such that a single-nucleotide change in the target RNA prevents the stem of the aptasensor from fully unwinding to expose the c domain. In SNP-specific Design 1 (FIG. 8A), domain c must fully open spontaneously to enable the aptamer to form. In SNP-specific Design 2 (FIG. 8B), a downstream c domain in the aptasensor can compete with the c/c* domains in the stem to promote aptamer formation. These SNP-specific systems could also provide sufficient specificity to enable detection of DNA and RNA modifications, for instance methylated RNAs.

Detection of Viral RNAs Using Broccoli-Based RNA Sensors: A series of Broccoli-based RNA sensors targeted to different viruses were developed using our aptasensor design algorithm. Two sets of sensors were designed for the human immunodeficiency virus (HIV) reverse transcriptase (RT) mRNA. These sensors detected the RNA sequence centered around two different regions of the HIV-RT mRNA: the K65 and Q151 residues. These two sites in HIV-RT have been associated with drug-resistant strains of the virus, and are thus useful locations to monitor in patients undergoing treatment and for implementing SNP-specific aptasensors. To characterize the HIV-RT sensors, we measured the fluorescence of the sensor RNAs upon exposure to high concentrations of the HIV-RT mRNA fragments of interest using the same procedures employed for the Pfs25 mRNA sensors shown in FIG. 5. Six different sensors for the two HIV-RT regions were tested. Analysis of the resulting fluorescence spectra yielded the ON/OFF ratios shown in FIG. 9. We found that multiple sensors for each mRNA region provided 23- to 53-fold increases in fluorescence. The fluorescence measured from these sensors indicate these systems can be coupled with RNA amplification schemes like NASBA to enable detection of the HIV virus from human samples.

Detection of Flavivirus and Related Virus RNAs Using Broccoli-Based RNA Sensors: Flaviviruses transmitted to humans via mosquito bites, and in some cases via sexual contact, have raised considerable worldwide concern as a result of the recent emergence of the Zika virus and its association with debilitating birth defects in fetuses exposed to the virus. A critical challenge in accurately identifying the Zika virus is its similarity to two other viruses, dengue and chikungunya, that are also transmitted by *Aedes aegypti* mosquitoes. Conventional serological assays have problems correctly identifying Zika infections in patients who have previously suffered dengue and chikungunya infections due to the similarity in antibody response to the viruses. Moreover, these infections elicit very similar symptoms in patients, further frustrating accurate diagnosis. As a result of these challenges, nucleic acid tests represent an essential method of identifying these viral infections during the acute stages of the illness.

We deployed our Broccoli-based RNA sensor design algorithm to the detection of RNAs from four different mosquito-borne viruses: the Zika strain from the Americas (ZIKV), the chikungunya virus (CHIKV), and dengue virus serotypes 1 (DENV1) and 3 (DENV3). In vitro transcription was used to produce sensor RNAs and to generate 120- to 176-nt regions from the RNA genomes of each virus. FIGS. 10A-10D present time course measurements of the fluorescence from sensors developed for the four different viruses. Each sensor was tested with and without its corresponding trigger RNA. Sensors were tested in triplicate and error bars reflect the standard deviation from the three measurements. In addition, the ZIKV and CHIKV sensors were also measured in comparison to a background buffer control. This buffer contained the DFHBI-1T dye, which exhibits low-level fluorescence even in the absence of the Broccoli aptamer. Accordingly, it provides a measure of the lower limit of fluorescence from the sensors. We found that the ZIKV (FIG. 10A) and CHIKV (FIG. 10B) sensors provided extremely low fluorescence leakage, nearly matching the fluorescence measured from the buffer background. These sensors also provided substantial increases in fluorescence upon exposure to viral RNA transcripts. The DENV1 and DENV3 sensors also yielded clear increases in fluorescence upon exposure to viral RNAs, albeit it at lower fluorescence intensities than for the other virus sensors. These results indicate that the Broccoli-based RNA sensors can also be employed for detection of mosquito-borne viruses from patient samples upon integration with isothermal amplification techniques like NASBA and RPA.

New Broccoli sensors for new targets: FIGS. 11A-11D show the response of multiple Broccoli-based sensors to target RNAs taken from the genomes of norovirus and the yellow fever virus. Target regions were selected for their high sequence conservation across multiple sequenced isolates for each virus. Each target was screened in the sense direction and the antisense direction since either strand polarity can be transcribed following amplification. The resulting four total target RNAs were used to screen six different Broccoli-based sensor designs. The results in FIGS. 11A-11D demonstrate that all four targets can elicit at least a 10-fold increase in fluorescence for one or more sensors. These sensors should thus be effective at identifying norovirus and the yellow fever virus in diagnostics.

As shown in FIGS. 12A-12B, dengue virus was detected Broccoli-based RNA sensors designed for detection of two different serotypes of dengue viruses: (A) dengue virus serotype 2 (DENV2), and (B) dengue virus serotype 4 (DENV4). These sensors should thus be effective at identifying two different serotypes of dengue virus in diagnostics.

Integrating Broccoli-based RNA sensors and RT-RPA-TX in one pot reactions: Recombinase polymerase amplification (RPA) is utilized for isothermal amplification of DNA. Three enzymes involved in the RPA reaction are recombinase, a single-stranded DNA-binding protein (SSB) and strand-displacing DNA polymerase. Recombinases form complexes with DNA primers and pair the primers with their homologous sequences in duplex DNA. SSB proteins bind to the displaced DNA strand while the DNA polymerases initiate DNA amplification from the primers. The amplification reaction progresses rapidly at 37° C. The addition of the reverse transcriptase and T7 polymerase allows amplification of RNA amplicons, conversion of Broccoli sensors from DNA to RNA and final target detection without the need for a separate step.

Figure 13C:
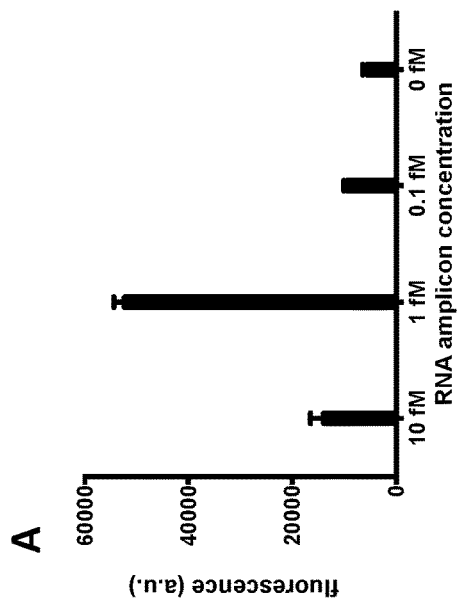
Figure 13D:
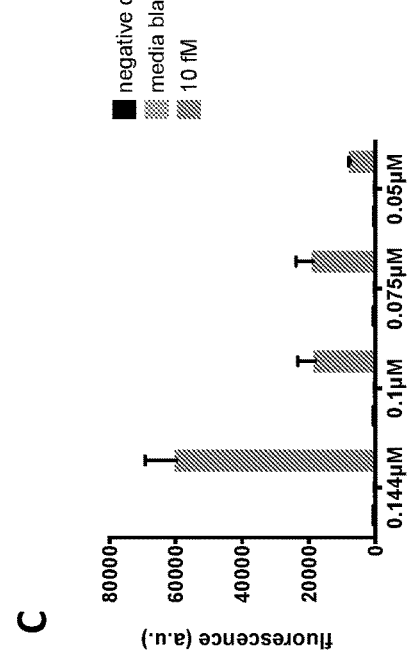

We first tested the integrated one-pot reaction for the amplification of the target RNA. We varied the concentration of the target RNA (Pfs25fwd target) at 10 fM, 1fM, 0.1 fM and 0 fM (with only the carrier molecule 10 μg/ml of tRNAs as negative control). The reactions proceeded for 2 hours at 37° C. Next, we incubated the 2μL reaction products with 2 μM of purified broccoli based RNA sensor (Pfs25fwd sensor) and DFHBI-1T buffer at a total volume of 10 μL for 1 hour at 37° C., and confirmed amplification of the target RNA via the fluorescence it induced from the Broccoli-based sensor. The 1 fM RNA amplicon input gave the highest fluorescence output (FIG. 13A), so we kept the target RNA at 1 fM and 10 fM, and replaced water with the DNA sensor template and 4 μM of DFHBI-1T for one-pot reactions that simultaneously amplified the target RNA and produced the RNA sensor. The reactions with the highest DNA sensor and RNA target concentrations gave the highest fluorescence signals (FIG. 13B). We performed reactions with non-target RNA as a negative control. The observed fluorescence leakage was extremely low compare with the media blank composed of the DFHBI-1T buffer (FIGS. 13C and 13D).

Utilizing Broccoli-based RNA sensors for detecting LAMP products: Loop-mediated isothermal amplification (LAMP) is an alternative method for the amplification of DNA. The reaction requires a DNA polymerase with strong strand displacement activity, 2 to 3 pairs of primers and a constant reaction temperature of 60 to 65° C. 4 or 6 primers will target 6 or 8 distinct regions within the target DNA, and will produce stem-loop DNA products. We selectively amplified a region (labeled PfMt869) of mitochondrial DNA of *P. falciparum*, and used the primer set listed in Table 1, and set loop regions of the amplified products as the targets for Broccoli-based sensors. The amplification reactions were carried out according to the manufacturer's instructions for Bst 2.0 DNA Polymerase (New England Biolabs) and were run for 30 minutes at 65° C.

TABLE 1

DNA Primer and Broccoli-Based RNA Sensor Sequences Used for LAMP Amplification and Detection of PfMt869

| | |
|---|---|
| F3 | CTCCATGTCGTCTCATCGC (SEQ ID NO: 5) |
| B3 | AACATTTTTTAGTCCCATGCTAA (SEQ ID NO: 6) |
| FIP | ACCCAGTATATTGATATTGCGTGACAGCCTTGCAATAAATAATA TCTAGC (SEQ ID NO: 7) |
| BIP | AACTCCAGGCGTTAACCTGTAATGATCTTTACGTTAAGGGC (SEQ ID NO: 8) |
| LF | CGGTGTGTACAAGGCAACAA (SEQ ID NO: 9) |
| LB | GTTGAGATGGAAACAGCCGG (SEQ ID NO: 10) |
| pT7_F2 | GCGC<u>TAATACGACTCACTATAGGG</u>AGCCTTGCAATAAATAATAT CTAGC (SEQ ID NO: 11) |
| pT7_B2 | GCGC<u>TAATACGACTCACTATAGGG</u>AATGATCTTTACGTTAAGGGC (SEQ ID NO: 12) |
| FL Sensor | GGGGUACAAGGCAACAAUACACGCUAGAUAUUAUUUAUCAUCCAC CAUACAUACUAUCUAGCGUGUUCGAGUAGAGUGUGGGCUCAGAUU CGUCUGAGACGGUCGGGUCACACGCUAG (SEQ ID NO: 13) |
| BL Sensor | GGGGAGUUGAGAUGGAAACAGCCGGAAAGGUAAUUUUACCAGCAU UUAACAUUACCUUUCCGGCUGUCGAGUAGAGUGUGGGCUCAGAUU CGUCUGAGACGGUCGGGUCCAGCCGGAAA (SEQ ID NO: 14) |

To increase the signal from the LAMP products in Broccoli-based sensor reactions, we added a second stage to the amplification reaction by adding 2 μM of either the pT7_F2 or the pT7_B2 primer to the reaction mixture. These primers contain T7 promoter sequences as shown by the underlined regions in Table 1. pT7_F2 or pT7_B2 also have the sequences used for binding to the target sequence in the standard LAMP primers FIP and BIP, respectively, as indicted by the bold regions in Table 1. The pT7_F2 primer thus can bind to part of the loop region in the LAMP amplicon and yield a DNA strand containing a T7 promoter immediately upstream of the LAMP amplicon sequence. This DNA strand can be displaced by extension of the BIP primer running in the opposite direction or 3' extension of the template strand. Displacement of the T7 promoter strand then enables its 3' end to fold back onto itself like in a typical LAMP reaction whereupon it is extended by the DNA polymerase. The end result of these steps is a fully double-stranded T7 promoter upstream of the amplicon sequence, which can be readily transcribed by T7 RNA polymerase in a subsequent detection reaction. Similarly, a conversion reaction employing pT7_B2 and the FIP primer will produce a LAMP product that can be transcribed in the opposite direction. These second stage reactions were run for 10 minutes at 65° C.

In vitro transcription reactions of 5 μL were then run with the LAMP-amplified target DNA product, sensor DNA template, and DFHBI-1T buffer for 3 hours at 37° C. inside a plate reader for fluorescence measurement. Both forward loop (FL) and backward loop (BL) Broccoli-based sensors activated within 1 hour of incubation (FIGS. 14A and 14B).

These FL and BL sensors detected portions of the loop of the LAMP amplicon downstream of the binding sites for pT7_F2 and pT7_B2 primers, respectively, which ensured that any residual primer could not cause false positive activation of the sensor. To determine the impact of transcription from the LAMP products modified to have T7 promoters, we tested the FL sensor against the standard LAMP DNA product (without pT7 primer in FIG. 14C) and the LAMP DNA product generated by the pT7_F2 primer (with pT7 primer in FIG. 14C). Equal volumes of the two products were added to in vitro transcription reactions with T7 RNA polymerase along with the DNA template for the Broccoli-based FL sensor. These experiments revealed that the Broccoli-based sensors can be turned on by either DNA target or their RNA targets as seen in FIG. 14C. As expected, we observed significantly higher fluorescence intensity for RNA targets compared to DNA targets since transcription likely produced multiple RNA copies for each LAMP DNA amplicon added to the reaction.

Discussion

Our Broccoli-based RNA sensors provide a dynamic range of fluorescence over 100-fold with very low leakage. These highly programmable sensors can be rationally programmed to detect any RNA sequence using custom design algorithms. We demonstrated that by coupling NASBA reactions with our Broccoli-based RNA sensors, we can detect pathogen-associated RNAs down to at least the 1 femtomolar range in simple one-pot reactions. When comparing our work with previously described workflows, Broccoli-based RNA sensors allow more rapid diagnostic tests at lower costs by eliminating the need for cell-free components.

The split bimolecular DNA enzyme probe developed by Dmitry M. Kolpashchikov relying on a colorimetric output allows visualization of single-nucleotide polymorphism typing. However, such binary DNA probe requires chemical incorporation of a triethylene glycol linker which is very costly. Moreover, the ON/OFF ratio for this probe was only ~10. Our unimolecular RNA sensors are easy to transcribe, amplify, and produce from more chemically stable DNA at point of care. Recently, Kikuchi and Kolpashchikov developed a similar split aptameric RNA probe using Spinach (another RNA mimic of GFP) with high selectivity at ambient temperatures and ON/OFF ratio up to 270-fold after 90 min of incubation. Once again, there was no demonstration for enzymatic production of their oligo probes. They also had overall lower fluorescent intensities at 37° C. due to less stable DFHBI-binding site of Spinach, so the probes might be less compatible with most enzymatic reactions and in vitro applications. Furthermore, it remains unclear how straightforward it is to design such split spinach probes for other target nucleic acid sequences. A common problem for split bimolecular probes is intramolecular folding based on the target nucleic acid binding sites. Such intramolecular folds can interfere with target binding to make probe use on diverse sequences challenging.

Broccoli-based RNA sensors and other aptasensors have many promising applications, especially for detection of pathogen-associated RNA in low resource settings. They could also find application for in-home use in the developed world, for instance for diagnosing the flu or cancer screening. Colorimetric outputs via new hemin-binding aptamer designs can provide direct visual detection without cell-free translation systems and without fluorescent excitation or optical filters. Previous work has shown that T7 RNA polymerase can be stably freeze-dried on paper and RNA amplification components can be freeze-dried and reconstituted as well. Thus, stably freeze-dried the RNA amplification and DFHBI-1T buffer components on paper or in test tubes will enable health providers to simply apply extracted RNA onto the test articles to rehydrate the resulting one-pot reactions for simple low-cost diagnostic tests.

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method of detecting a target nucleic acid, the method comprising the steps of:
   (a) obtaining nucleic acids from a biological sample of a subject;
   (b) amplifying the nucleic acids using isothermal amplification;
   (c) contacting the amplified nucleic acids to a unimolecular aptamer-based sensor,
      wherein the unimolecular aptamer-based sensor is a nucleic acid sequence comprising one or more single-stranded toehold sequence domains that are designed to be fully complementary to the target nucleic acid, a stem-loop domain downstream of the one or more toehold sequence domains, and a single-stranded aptamer domain comprising an aptamer sequence downstream of the stem-loop domain,
      wherein the stem-loop domain comprises a loop and an at least partially double-stranded stem,
      wherein at least a portion of the stem-loop domain is complementary to the aptamer sequence, and
      wherein the contacting occurs under conditions that promote unwinding of the stem domain and activation of an aptamer-ligand complex in the presence of the target nucleic acid; and
   (d) detecting fluorescence emitted or color produced by the ligand in the activated aptamer-ligand complex as an indicator that the target nucleic acid is present in the sample.

2. The method of claim 1, wherein the aptamer-ligand complex comprises an aptamer selected from the group consisting of a Broccoli aptamer comprising SEQ ID NO:3 or SEQ ID NO: 4, a G-quadruplex-containing aptamer, and a malachite green binding aptamer.

3. The method of claim 1, wherein the target nucleic acid comprises RNA or DNA.

4. The method of claim 1, wherein the unimolecular aptamer-based sensor further comprises a second aptamer domain comprising a second aptamer sequence, wherein the second aptamer sequence is located in the loop.

5. The method of claim 1, wherein the sample is a biological sample selected from the group consisting of blood, plasma, serum, urine, saliva, tissue, cell, organ, and organism, or a portion thereof.

6. The method of claim 1, wherein the isothermal amplification is a method selected from the group consisting of NASBA (nucleic acid sequence-based amplification), LAMP (loop-mediated isothermal amplification), and RPA (recombinase polymerase amplification).

7. A method of detecting presence of pathogen-associated nucleic acid in a sample, the method comprising the steps of:
   (a) obtaining nucleic acids from a biological sample of a subject;
   (b) amplifying the nucleic acids using isothermal amplification; and
   (c) contacting the amplified nucleic acids to a unimolecular aptamer-based sensor,
      wherein the unimolecular aptamer-based sensor is a nucleic acid sequence comprising one or more single-stranded toehold sequence domains that are designed to be fully complementary to the target pathogen-associated nucleic acid, a stem-loop domain downstream of the one or more toehold sequence domains, and a single-stranded aptamer domain comprising an aptamer sequence downstream of the stem-loop domain,
      wherein the stem-loop domain comprises a loop and an at least partially double-stranded stem,
      wherein at least a portion of the stem-loop domain is complementary to the aptamer sequence, and
      wherein the contacting occurs under conditions that promote unwinding of the stem domain and activation of an aptamer-ligand complex in the presence of the target pathogen-associated nucleic acid but not in the absence of the pathogen-associated nucleic acid, and
   (d) detecting fluorescence emitted or color produced by the ligand in the activated aptamer-ligand complex as an indicator that the target nucleic acid is present in the sample.

8. The method of claim 7, wherein the aptamer-ligand complex comprises an aptamer selected from the group consisting of a Broccoli aptamer comprising SEQ ID NO: 3 or SEQ ID NO: 4, a G-quadruplex-containing aptamer, and a malachite green binding aptamer.

9. The method of claim 7, wherein the target nucleic acid comprises RNA or DNA.

10. The method of claim 7, wherein the isothermal amplification is a method selected from the group consisting of NASBA, LAMP, and RPA.

11. The method of claim 7, wherein the sample is a biological sample selected from the group consisting of blood, plasma, serum, urine, saliva, tissue, cell, organ, and organism, or a portion thereof.

12. The method of claim 7, wherein the unimolecular aptamer-based sensor further comprises a second aptamer domain comprising a second aptamer sequence, the second aptamer sequence is located in the loop.

* * * * *

```
                         SEQUENCE LISTING

<160> NUMBER OF SEQ ID NOS: 14

<210> SEQ ID NO 1
  <211> LENGTH: 17
  <212> TYPE: RNA
  <213> ORGANISM: Artificial Sequence
  <220> FEATURE:
  <223> OTHER INFORMATION: Broccoli domain X aptamer

<400> SEQUENCE: 1
ucugagacgg ucggguc                                                   17

<210> SEQ ID NO 2
  <211> LENGTH: 22
  <212> TYPE: RNA
  <213> ORGANISM: Artificial Sequence
  <220> FEATURE:
  <223> OTHER INFORMATION: Broccoli domain Y aptamer

<400> SEQUENCE: 2
ucgaguagag ugugggcuca ga                                             22

<210> SEQ ID NO 3
  <211> LENGTH: 55
  <212> TYPE: RNA
  <213> ORGANISM: Artificial Sequence
  <220> FEATURE:
  <223> OTHER INFORMATION: Standard Broccoli configuration

<400> SEQUENCE: 3
ucugagacgg ucggguccag auauucguau cgucgagua gagugugggc ucaga          55

<210> SEQ ID NO 4
  <211> LENGTH: 55
  <212> TYPE: RNA
  <213> ORGANISM: Artificial Sequence
  <220> FEATURE:
  <223> OTHER INFORMATION: Rotated Broccoli configuration

<400> SEQUENCE: 4
uaucugucga guagagugug ggcucagauu cgucugagac ggucgggucc agaua          55

<210> SEQ ID NO 5
  <211> LENGTH: 19
  <212> TYPE: DNA
  <213> ORGANISM: Artificial Sequence
  <220> FEATURE:
  <223> OTHER INFORMATION: F3 primer

<400> SEQUENCE: 5
ctccatgtcg tctcatcgc                                                 19

<210> SEQ ID NO 6
  <211> LENGTH: 23
  <212> TYPE: DNA
  <213> ORGANISM: Artificial Sequence
  <220> FEATURE:
  <223> OTHER INFORMATION: B3 primer
```

<400> SEQUENCE: 6
aacatttttt agtcccatgc taa                                          23

<210> SEQ ID NO 7
<211> LENGTH: 50
<212> TYPE: DNA
<213> ORGANISM: Artificial Sequence
<220> FEATURE:
<223> OTHER INFORMATION: FIP primer

<400> SEQUENCE: 7
acccagtata ttgatattgc gtgacagcct tgcaataaat aatatctagc              50

<210> SEQ ID NO 8
<211> LENGTH: 41
<212> TYPE: DNA
<213> ORGANISM: Artificial Sequence
<220> FEATURE:
<223> OTHER INFORMATION: BIP primer

<400> SEQUENCE: 8
aactccaggc gttaacctgt aatgatcttt acgttaaggg c                      41

<210> SEQ ID NO 9
<211> LENGTH: 20
<212> TYPE: DNA
<213> ORGANISM: Artificial Sequence
<220> FEATURE:
<223> OTHER INFORMATION: LF primer

<400> SEQUENCE: 9
cggtgtgtac aaggcaacaa                                              20

<210> SEQ ID NO 10
<211> LENGTH: 20
<212> TYPE: DNA
<213> ORGANISM: Artificial Sequence
<220> FEATURE:
<223> OTHER INFORMATION: LB primer

<400> SEQUENCE: 10
gttgagatgg aaacagccgg                                              20

<210> SEQ ID NO 11
<211> LENGTH: 49
<212> TYPE: DNA
<213> ORGANISM: Artificial Sequence
<220> FEATURE:
<223> OTHER INFORMATION: pT7_F2 primer

<400> SEQUENCE: 11
gcgctaatac gactcactat agggagcctt gcaataaata atatctagc               49

<210> SEQ ID NO 12
<211> LENGTH: 45
<212> TYPE: DNA
<213> ORGANISM: Artificial Sequence
<220> FEATURE:
<223> OTHER INFORMATION: pT7_B2 primer

<400> SEQUENCE: 12
gcgctaatac gactcactat agggaatgat ctttacgtta agggc                   45

<210> SEQ ID NO 13

```
<211> LENGTH: 118
<212> TYPE: RNA
<213> ORGANISM: Artificial Sequence
<220> FEATURE:
<223> OTHER INFORMATION: FL sensor

<400> SEQUENCE: 13
gggguacaag gcaacaauac acgcuagaua uuauuuauca uccaccauac auacuaucua     60
gcguguucga guagagugug ggcucagauu cgucugagac ggucgggguca cacgcuag    118

<210> SEQ ID NO 14
<211> LENGTH: 119
<212> TYPE: RNA
<213> ORGANISM: Artificial Sequence
<220> FEATURE:
<223> OTHER INFORMATION: BL sensor

<400> SEQUENCE: 14
ggggaguuga gauggaaaca gccggaaagg uaauuuacc agcauuuaac auuaccuuuc      60
cggcugucga guagagugug ggcucagauu cgucugagac ggucgggucc agccggaaa    119
```